United States Patent
Caizza et al.

(10) Patent No.: US 8,920,371 B2
(45) Date of Patent: Dec. 30, 2014

(54) SYRINGE WITH DISABLING MECHANISM

(71) Applicant: Becton, Dickinson and Company, Franklin Lakes, NJ (US)

(72) Inventors: Richard J. Caizza, Vernon, NJ (US); Robert B. Odell, Franklin Lakes, NJ (US); Brian H. Wayman, Morris Plains, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 8 days.

(21) Appl. No.: 13/719,325

(22) Filed: Dec. 19, 2012

(65) Prior Publication Data

US 2013/0110044 A1     May 2, 2013

Related U.S. Application Data

(63) Continuation of application No. 12/885,842, filed on Sep. 20, 2010, now Pat. No. 8,361,018, which is a continuation-in-part of application No. 12/262,836, filed on Oct. 31, 2008, now Pat. No. 7,972,304, which is a continuation-in-part of application No. 12/137,732, filed on Jun. 12, 2008, now Pat. No. 7,972,302.

(60) Provisional application No. 60/943,397, filed on Jun. 12, 2007.

(51) Int. Cl.
*A61M 5/00* (2006.01)
*A61M 5/50* (2006.01)
*A61M 5/315* (2006.01)
*A61M 5/31* (2006.01)

(52) U.S. Cl.
CPC ......... *A61M 5/50* (2013.01); *A61M 2005/5073* (2013.01); *A61M 2005/31516* (2013.01); *A61M 5/502* (2013.01); *A61M 5/3135* (2013.01); *A61M 2005/5026* (2013.01); *A61M 5/5066* (2013.01)
USPC ............ 604/110; 604/218; 604/220; 604/225

(58) Field of Classification Search
CPC ......... A61M 5/00; A61M 5/31; A61M 5/315; A61M 5/322; A61M 5/3234; A61M 5/31511; A61M 5/31513; A61M 5/31505
USPC .................................. 604/110, 218, 220, 225
See application file for complete search history.

(56) References Cited

U.S. PATENT DOCUMENTS

| 4,367,738 | A | 1/1983 | Legendre et al. |
| 4,775,363 | A | 10/1988 | Sandsdalen |

(Continued)

FOREIGN PATENT DOCUMENTS

| BE | 1001579 | 12/1989 |
| CA | 1306397 | 8/1992 |

(Continued)

OTHER PUBLICATIONS

"Final Office Action in U.S. Appl. No. 12/137,732, dated Dec. 22, 2010", 27 pgs.

(Continued)

*Primary Examiner* — Scott Medway
(74) *Attorney, Agent, or Firm* — Servilla Whitney LLC

(57) ABSTRACT

Syringe assemblies having a passive disabling system to prevent reuse are provided. According to one or more embodiments, the syringe assembly comprises a barrel, plunger rod and stopper wherein the plunger rod further comprises a flexible protrusion that locks the plunger rod within the barrel. Certain embodiments further include a frangible portion on the plunger rod that breaks when reuse is attempted.

27 Claims, 40 Drawing Sheets

(56) References Cited

U.S. PATENT DOCUMENTS

| | | | |
|---|---|---|---|
| 4,915,692 A | 4/1990 | Verlier | |
| 4,932,941 A | 6/1990 | Min et al. | |
| 4,973,310 A | 11/1990 | Kosinski | |
| 5,047,017 A | 9/1991 | Koska | |
| 5,053,010 A | 10/1991 | McGary et al. | |
| 5,106,372 A | 4/1992 | Ranford | |
| 5,114,405 A | 5/1992 | Winter | |
| 5,116,320 A | 5/1992 | Lo Duca | |
| 5,188,616 A | 2/1993 | Nadal | |
| 5,211,629 A | 5/1993 | Pressly et al. | |
| 5,269,760 A | 12/1993 | Bina | |
| 5,370,620 A | 12/1994 | Shonfeld | |
| 5,395,346 A | 3/1995 | Maggioni | |
| 5,531,693 A | 7/1996 | Vounatsos | |
| 5,989,219 A | 11/1999 | Villas et al. | |
| 6,090,077 A | 7/2000 | Shaw | |
| 6,368,306 B1 | 4/2002 | Koska | |
| 6,599,269 B1 | 7/2003 | Lewandowski et al. | |
| 7,387,615 B2 | 6/2008 | Coelho et al. | |
| 2003/0032928 A1 | 2/2003 | Sudo et al. | |
| 2004/0176722 A1 | 9/2004 | Capes et al. | |
| 2005/0027250 A1 | 2/2005 | Suresh et al. | |
| 2006/0052748 A1 | 3/2006 | Coelho et al. | |
| 2006/0173411 A1 | 8/2006 | Barere | |
| 2009/0018510 A1 | 1/2009 | Madin et al. | |
| 2009/0048560 A1 | 2/2009 | Caizza et al. | |
| 2009/0131869 A1 | 5/2009 | Caizza et al. | |
| 2009/0198194 A1 | 8/2009 | Madin et al. | |
| 2010/0268160 A1 | 10/2010 | Eccard | |

FOREIGN PATENT DOCUMENTS

| | | |
|---|---|---|
| CN | 1035244 | 9/1989 |
| CN | 1713932 | 12/2005 |
| CN | 2936285 | 8/2007 |
| CN | 101087627 | 12/2007 |
| EP | 0340899 | 11/1989 |
| EP | 1106194 | 6/2001 |
| FR | 2625439 | 7/1989 |
| FR | 2686517 | 7/1993 |
| FR | 2689765 | 10/1993 |
| GB | 2197792 | 6/1988 |
| JP | 11089933 | 4/1999 |
| WO | WO-89/06146 | 7/1989 |
| WO | WO-90/03818 | 4/1990 |
| WO | WO-01/64266 | 9/2001 |
| WO | WO-03/037411 | 5/2003 |
| WO | WO-2004/033008 | 4/2004 |
| WO | WO-2004/045683 | 6/2004 |
| WO | WO-2006/068650 | 6/2006 |
| WO | WO-2008/148534 | 12/2008 |
| WO | WO-2008/154616 | 12/2008 |
| WO | WO-2009/151472 | 12/2009 |

OTHER PUBLICATIONS

"Final Office Action in U.S. Appl. No. 12/137,854, dated Dec. 22, 2010", 20 pgs.

"Final Office Action in U.S. Appl. No. 12/262,836, dated Dec. 27, 2010", 25 pgs.

"Non-Final Office Action", U.S. Appl. No. 12/137,854 Feb. 4, 2010, 14 pgs.

"Non-Final Office Action", U.S. Appl. No. 12/137,854 Feb. 4, 2008, 15.

"Non-Final Office Action", U.S. Appl. No. 12/262,836 Feb. 4, 2010, 16 pgs.

"Non-Final Office Action", U.S. Appl. No. 12,137,854 Jul. 21, 2010, 17.

"Non-Final Office Action", U.S. Appl. No. 137,732 Feb. 4, 2010, 18.

"Non-Final Office Action", U.S. Appl. No. 12/137,732 Jul. 21, 2010, 22.

"Non-Final Office Action", U.S. Appl. No. 12/262,836 Jul. 22, 2010, 22.

"Non-Final Office Action in U.S. Appl. No. 12/137,732, mailed Feb. 4, 2010,", 18 pgs.

"Notice of Refs Cited (892)", NFOA Feb. 4, 2010 in U.S. Appl. No. 12/262,836 Feb. 4, 2010, 1 pg.

"PCT International Search Report & Written Opinion in PCT/US2011/051947, dated Feb. 8, 2012",, 13 pgs.

"PCT Search Report", PCT/US/2008/066655 Sep. 19, 2008, 2 pgs.

"PCT Search Report", PCT/US08/66705 Jan. 30, 2009, 3 pgs.

"PCT Search Report & Written Opinion", PCT/US08/82045 May 6, 2009, 14 pgs.

"PCT Written Opinion", PCT/US2008/066655 Sep. 19, 2008, 5 pgs.

"PCT Written Opinion", PCT/US08/66705 Jan. 30, 2009, 8 pgs.

Official Notice of Rejection, mailed on Feb. 19, 2013, for Japanese Patent Application No. 2011-513474, which corresponds to this patent application.

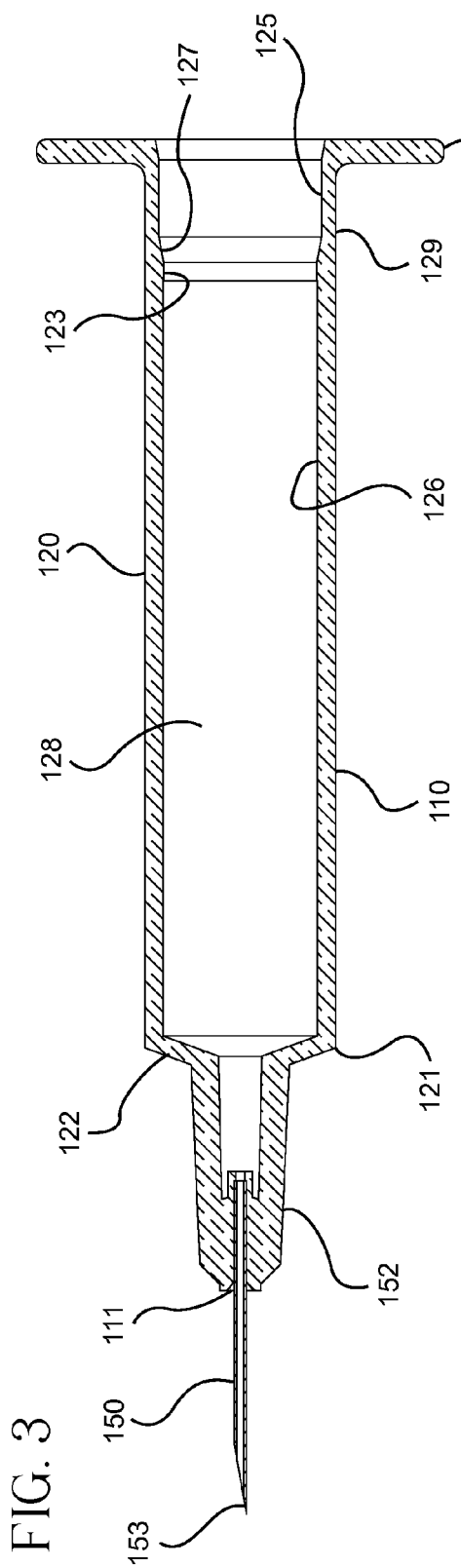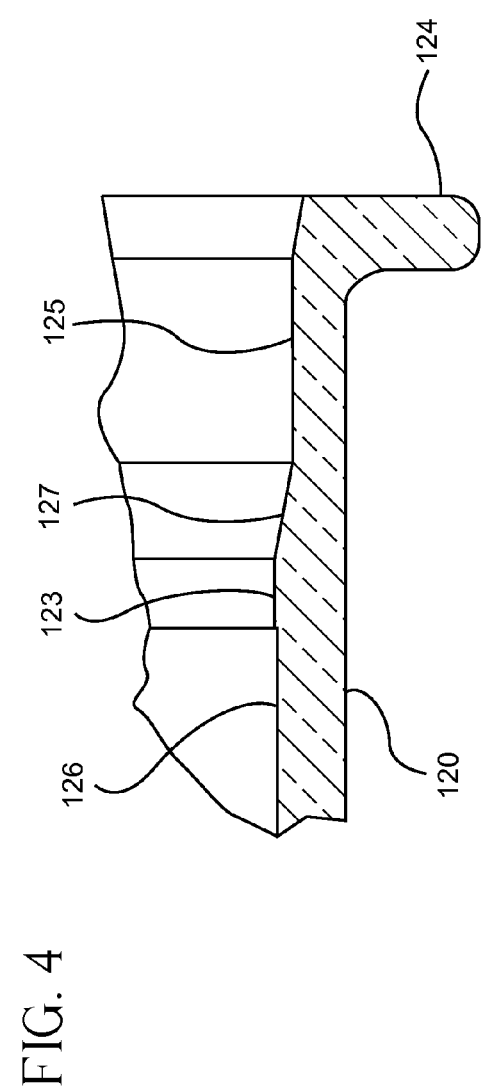

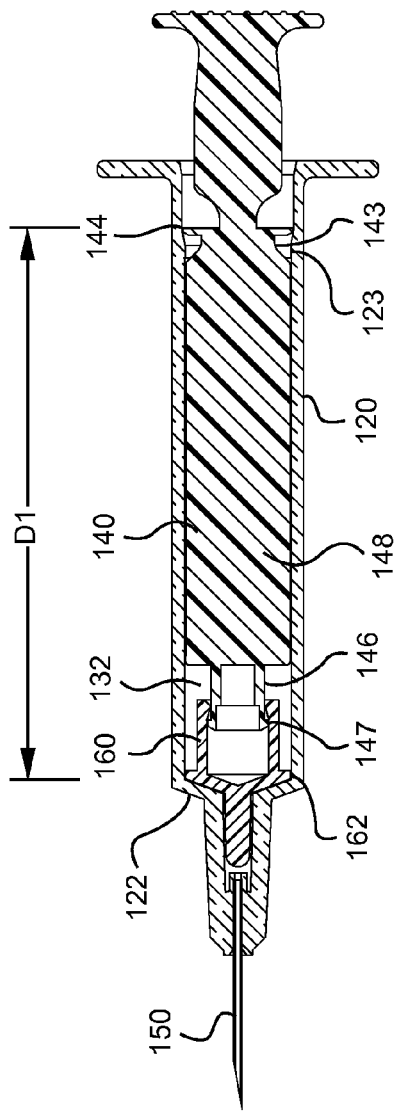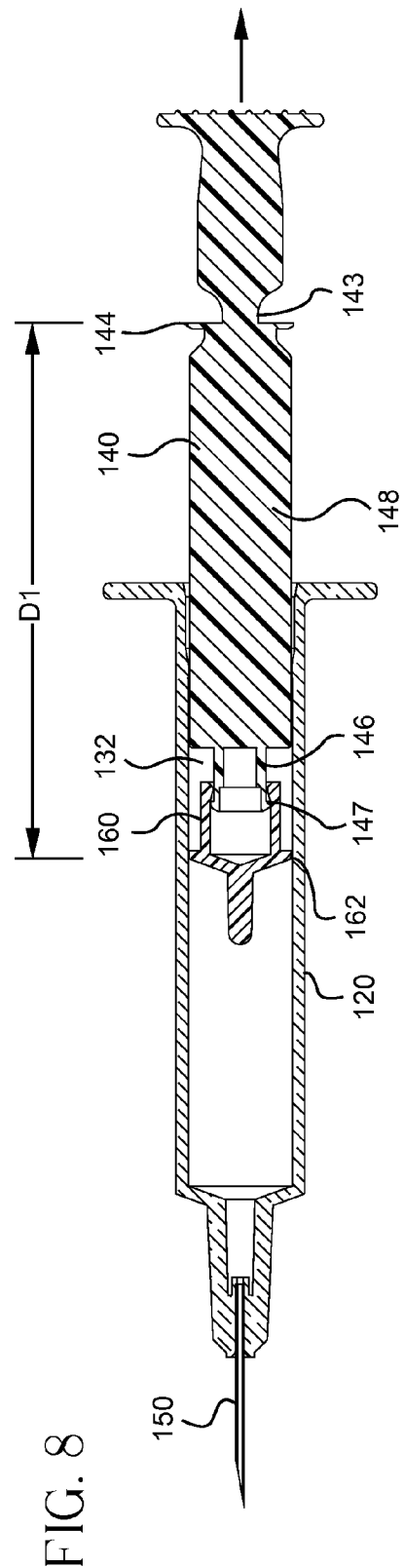
FIG. 7
FIG. 8

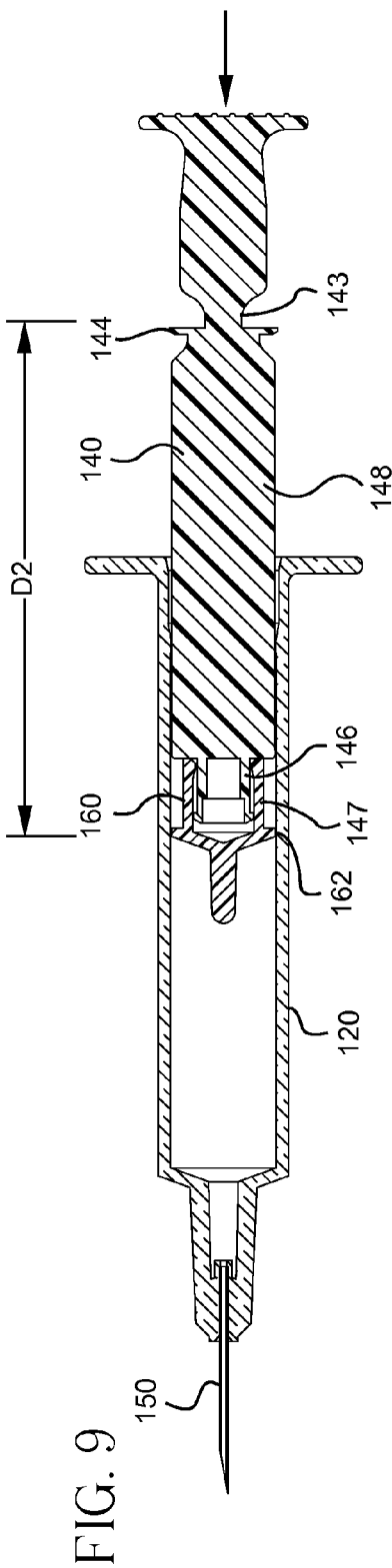
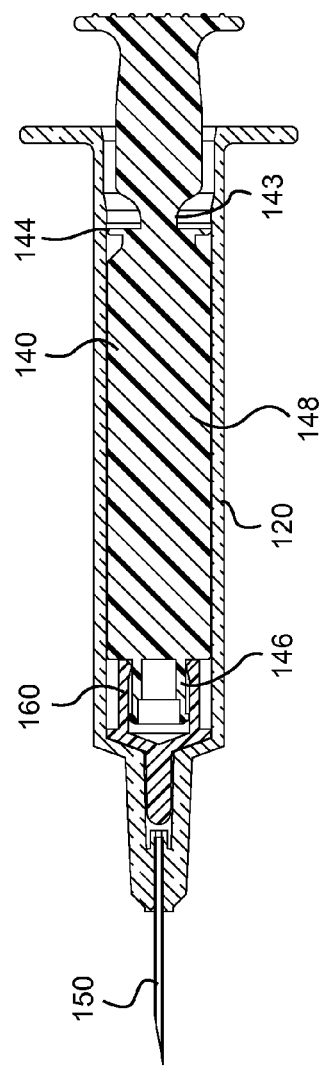
FIG. 9
FIG. 10

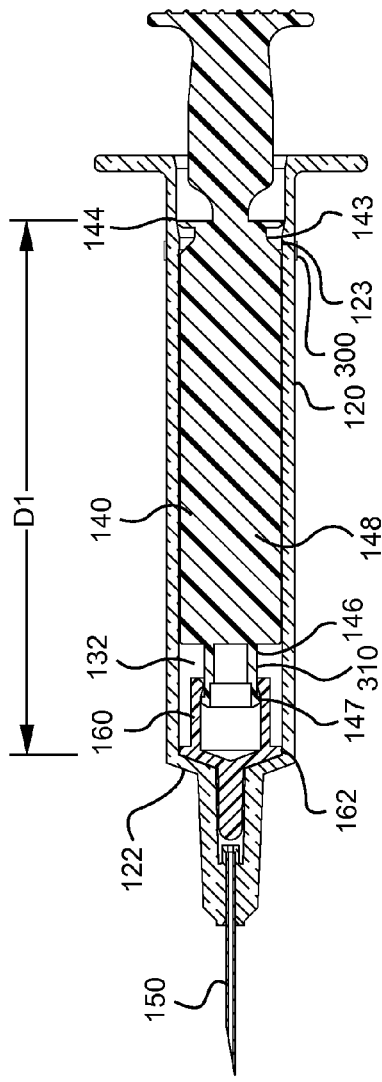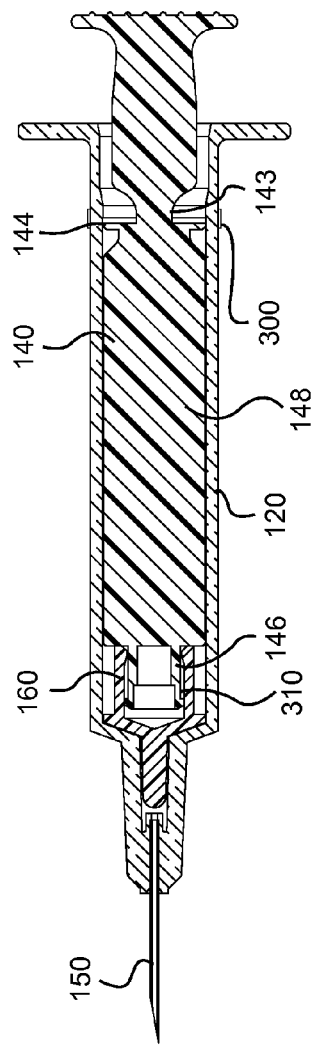
FIG. 14
FIG. 15

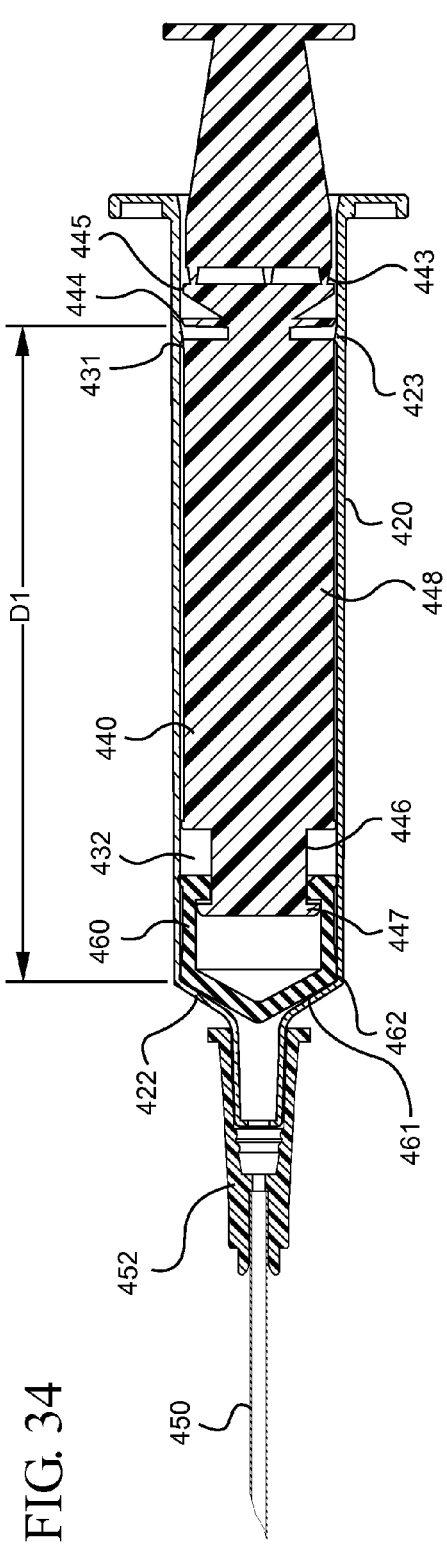
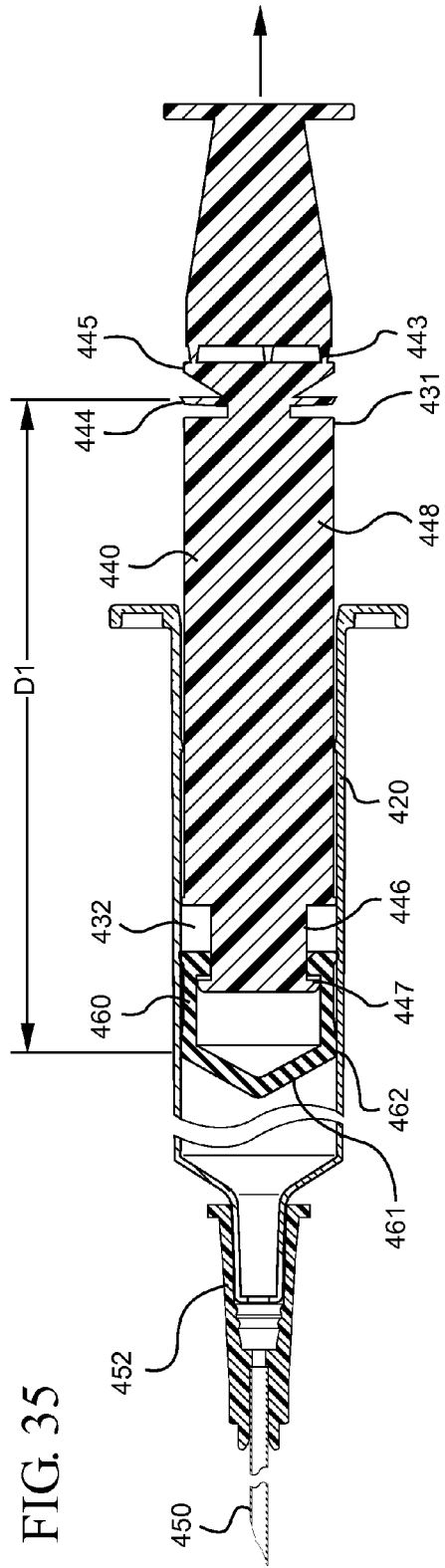

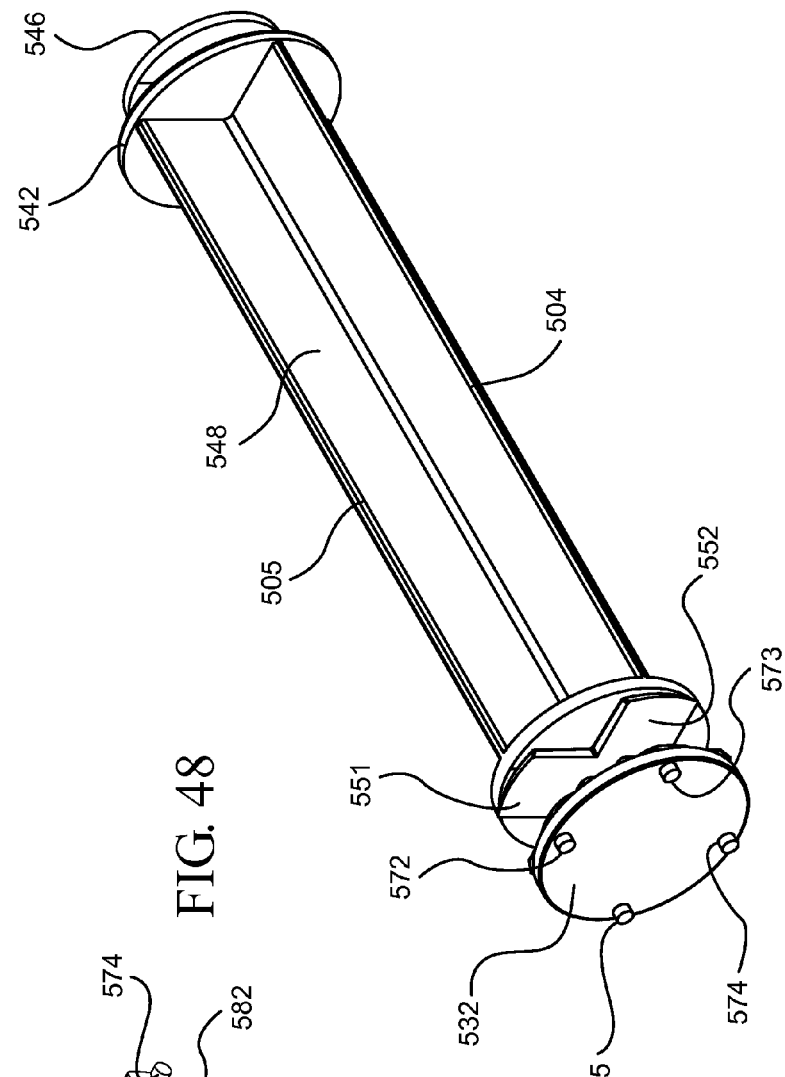
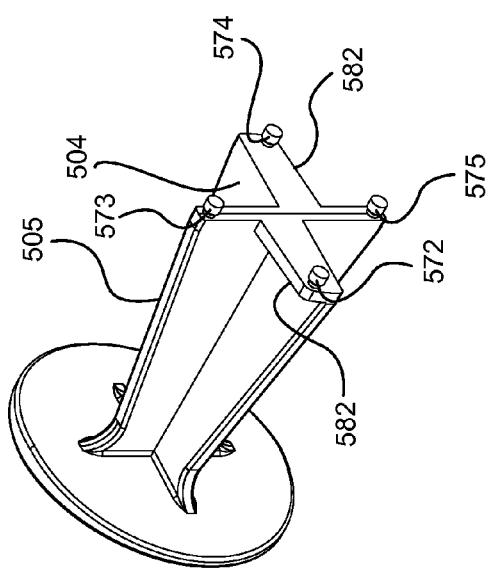
FIG. 47
FIG. 48

SYRINGE WITH DISABLING MECHANISM

CROSS-REFERENCE TO RELATED APPLICATIONS

This application is a continuation of U.S. patent application Ser. No. 12/885,842 filed Sep. 20, 2010, which is a continuation-in-part of U.S. patent application Ser. No. 12/262,836 filed Oct. 31, 2008, which is a continuation-in-part of U.S. patent application Ser. No. 12/137,732, filed Jun. 12, 2008, which claims the benefit of priority from U.S. Provisional Application No. 60/943,397, filed Jun. 12, 2007, the disclosures of which are hereby incorporated in its entirety by reference thereto.

TECHNICAL FIELD

Embodiments of the present invention relate to syringe assemblies having a passive locking mechanism which restricts distal movement of the plunger rod after injection to prevent reuse, syringe assemblies wherein the stopper and plunger rod operate using relative motion to passively disable the syringe, syringe assemblies including a removeably connected stopper and plunger rod to prevent disassembly of the syringe prior to use and syringe assemblies including visual indication or markings to indicate use of the syringe or a disabled syringe.

BACKGROUND

Reuse of hypodermic syringe products without sterilization or sufficient sterilization is believed to perpetuate drug abuse and facilitate the transfer of contagious diseases. The reuse of syringes by intravenous drug users further exacerbates the transfer of contagious diseases because they comprise a high-risk group with respect to certain viruses such as the AIDS virus and hepatitis. A high risk of contamination also exists in countries with shortages of medical personnel and supplies.

A syringe which can be rendered inoperable after use presents a viable solution to these issues. Various syringes have been proposed and are commercially available that can be disabled by the user by taking active steps to disable the syringe. Single-use syringes that do not require the user to actively disable the syringe are also thought to offer a solution. It would be desirable to provide syringes that are automatically or passively disabled from reuse and can be manufactured in a cost-effective manner by, for example, utilizing fewer parts. Further, markings or other indicators which visually indicate whether a syringe has been used or is disabled would also be desirable.

SUMMARY

A passive disabling system for a syringe assembly that activates after completion of an injection cycle is provided. A syringe assembly incorporates a stopper and plunger rod attached in a manner to prevent users from disassembling the syringe prior to completion of the injection cycle. In one or more embodiments of the invention, a user can fill, inject and/or reconstitute medication.

In this disclosure, a convention is followed wherein the distal end of the device is the end closest to a patient and the proximal end of the device is the end away from the patient and closest to a practitioner. The term "diameter" is a measurement of the longest distance between the walls of the barrel having any cross-sectional shape and may be used interchangeably with the term cross-sectional width.

A syringe assembly is provided which includes a barrel, an elongate plunger rod and stopper having respective structures and assembly which allow the user to passively lock the plunger rod within the barrel to prevent reuse of the syringe assembly. The barrel includes a distal end, an open proximal end, a cylindrical sidewall with an interior surface, which defines a chamber in which fluid may be held, and a distal wall. The interior surface also defines a first cross-sectional width. An opening in the distal wall permits fluid to flow from the chamber through the opening.

In one or more embodiments, the interior surface of the sidewall of the barrel includes a rib adjacent to the proximal end. The rib defines a second cross-sectional width that is less than the first cross-sectional width defined at the remaining portions of the interior surface. The rib forms an impediment for restricting the proximal movement of the plunger rod.

Embodiments of the present invention also include an extended plunger rod which has a proximal end, a distal end, and a main body between the proximal and distal end. A thumb press may also be disposed at the proximal end of the plunger rod. In some embodiments, the plunger rod slides or otherwise moves proximally and distally within the chamber of the barrel.

The distal end of the plunger may include a stopper-engaging portion having a distal and proximal end. The plunger rod also includes a flexible protrusion that is disposed between the thumb press and the main body of the plunger rod. The flexible protrusion of one or more embodiments includes a cross-sectional width that is greater than the second cross-sectional width or the cross-sectional width of the barrel at the rib. In one or more alternative embodiments, the plunger rod may include a support member that includes an outer edge. The support member may be disposed proximally adjacent to the flexible protrusion. In one or more alternative embodiments, the plunger rod may include a first support member disposed perpendicularly to the plunger rod that includes an annular projection having a distally facing surface, a proximally facing surface and an outer edge. A strut element may be disposed on the distally facing surface between the flexible protrusion and the annular projection. The flexible protrusion of one or more embodiments facilitates distal movement of the plunger rod by flexing in the proximal direction as a force is applied in the distal direction to the plunger rod. The plunger rod may also include a frangible portion that is disposed proximally adjacent to the support member. The frangible portion may include two or more point connections disposed adjacent to the edge of the support member.

In one or more specific embodiments, the frangible portion may include three point connections that may be spaced equidistant from each other. In a more specific embodiment, the frangible portion may include at least four point connections. In one even more specific embodiment, a first and a second of the four point connections may be disposed equidistant from each other and the third and fourth of the four point connections are also disposed equidistant from each other. In variant, all four point connections are disposed equidistant from each other. In another variant, the distance between the first and second point connections is greater than the distance between the third and fourth point connections.

In one or more embodiments, the flexible protrusions include at least two leaves extending radially outwardly from the plunger rod. In one or more alternative embodiments, the flexible protrusion includes more than two leaves, which may be equidistant from each other or may be disposed at different distances from each other. The point connections of the frangible portion may be aligned with the leaves. In one or more embodiments, the protrusion includes four leaves disposed equidistant from each other. In such embodiments, the frangible portion may include four point connections in which the first and the second are aligned with the first and the second leaves, while the third point connection and fourth point connection are misaligned with the third and the fourth leaves, wherein the third point connection and the fourth point connection are disposed adjacent to opposite ends of the outer edge of the support member.

A syringe assembly of one or more embodiments may include a stopper including a proximal end and a distal end. The stopper may be attached to the stopper-engaging portion of the plunger rod such that when the stopper is in contact with the distal wall of the barrel, the flexible protrusion is permitted to advance distally past the rib and lock the plunger rod in the barrel to prevent reuse of the syringe assembly. Specifically, when the stopper is in contact with the distal wall of the barrel, the flexible protrusion of the plunger rod moves or advances distally past the rib of the barrel.

In one or more embodiments, the stopper and plunger rod are disposed within the barrel when the syringe assembly is in an initial position such that there is a gap between the distal end of the stopper and the distal wall of the barrel. In one or more embodiments, the application of a force in the distal direction to the plunger rod causes the stopper and the plunger rod to move together in the distal direction until the stopper reaches the distal end of the barrel, thereby allowing the protrusion to advance distally past the rib in the barrel and lock the plunger rod in the barrel to prevent reuse of the syringe assembly. After the plunger rod has been locked in the barrel, the application of a proximally directed force to the plunger rod causes the frangible portion of the plunger rod to break.

In one or more embodiments, the two or more point connections of the frangible portion are adapted to withstand application of a force on the plunger rod in the distal direction and break upon application of a force in the proximal direction after the flexible protrusion has advanced distally past the rib. In one or more embodiments, the force required to move the plunger rod in the proximal direction after the flexible protrusion has advanced distally past the rib exceeds the force required to break the two or more point connections.

BRIEF DESCRIPTION OF THE DRAWINGS

FIG. 3 shows a cross-sectional view of the barrel shown in FIG. 2 taken along line 3-3;

FIG. 4 is an enlarged view of a portion of the barrel shown in FIG. 3;

FIG. 7 is a cross-sectional view taken along line 7-7 of FIG. 1;

FIG. 8 is an illustration of FIG. 7 showing the plunger rod being moved in the proximal direction;

FIG. 9 is an illustration of FIG. 8 showing the plunger rod being moved in the distal direction;

FIG. 10 is an illustration of FIG. 9 showing the plunger rod in a locked position in the syringe barrel;

FIG. 14 is a cross-sectional view taken along line 14-14 of FIG. 12;

FIG. 15 is an illustration of FIG. 14 showing the plunger rod in a locked position in the syringe barrel;

FIG. 34 is a cross-sectional view taken along line 34-34 of the syringe assembly shown in FIG. 28;

FIG. 35 is an illustration of FIG. 34 showing the plunger rod being moved in the proximal direction;

FIG. 47 illustrates a partial perspective view of a portion of the plunger rod shown in FIG. 45 distally adjacent to the frangible portion;

FIG. 48 illustrates a partial perspective view of a portion of the plunger rod shown in FIG. 45 proximally adjacent to the frangible portion;

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

One aspect of the present invention provides for a syringe assembly including a barrel, plunger rod and stopper having individual features and construction which allow the user to passively lock the plunger rod within the barrel to prevent reuse of the syringe assembly.

Figure 1:
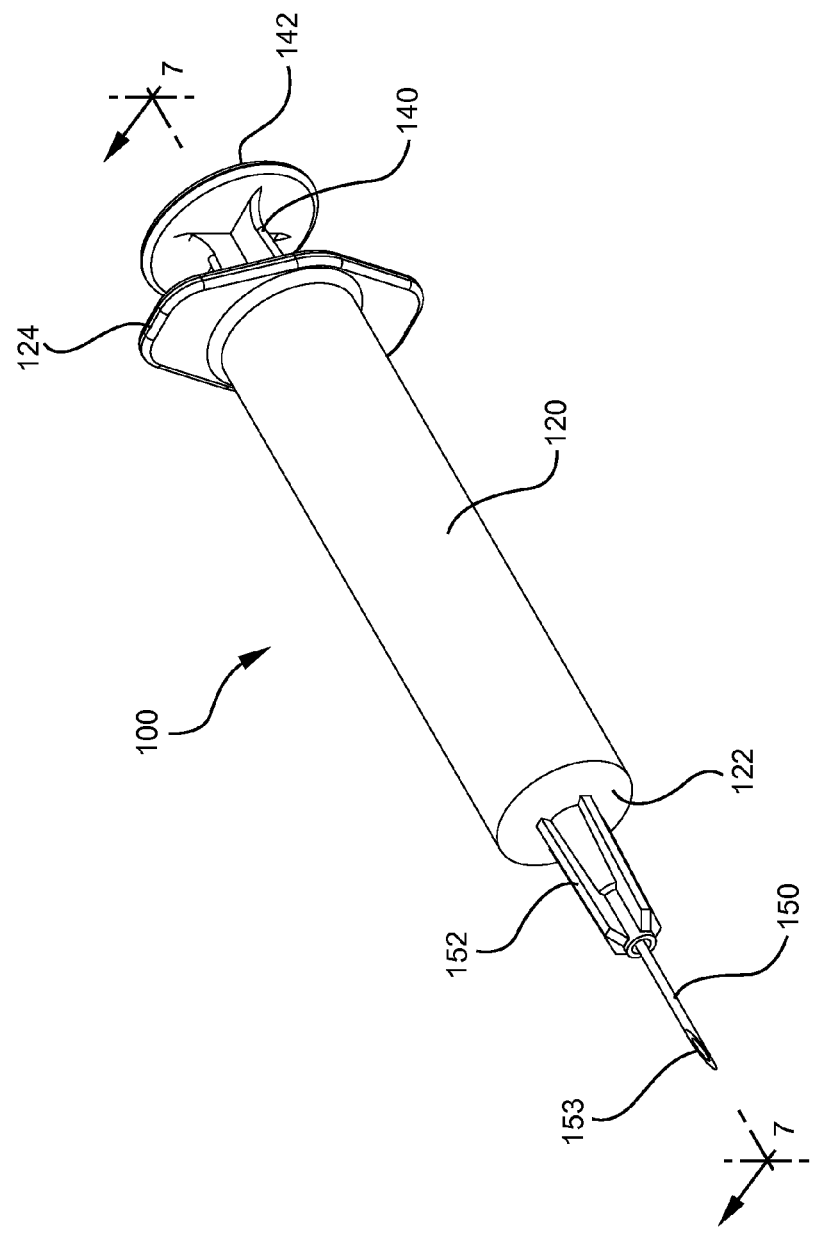
FIG. 1 illustrates a perspective view of a syringe assembly according to an embodiment of the invention shown.
Figure 2:
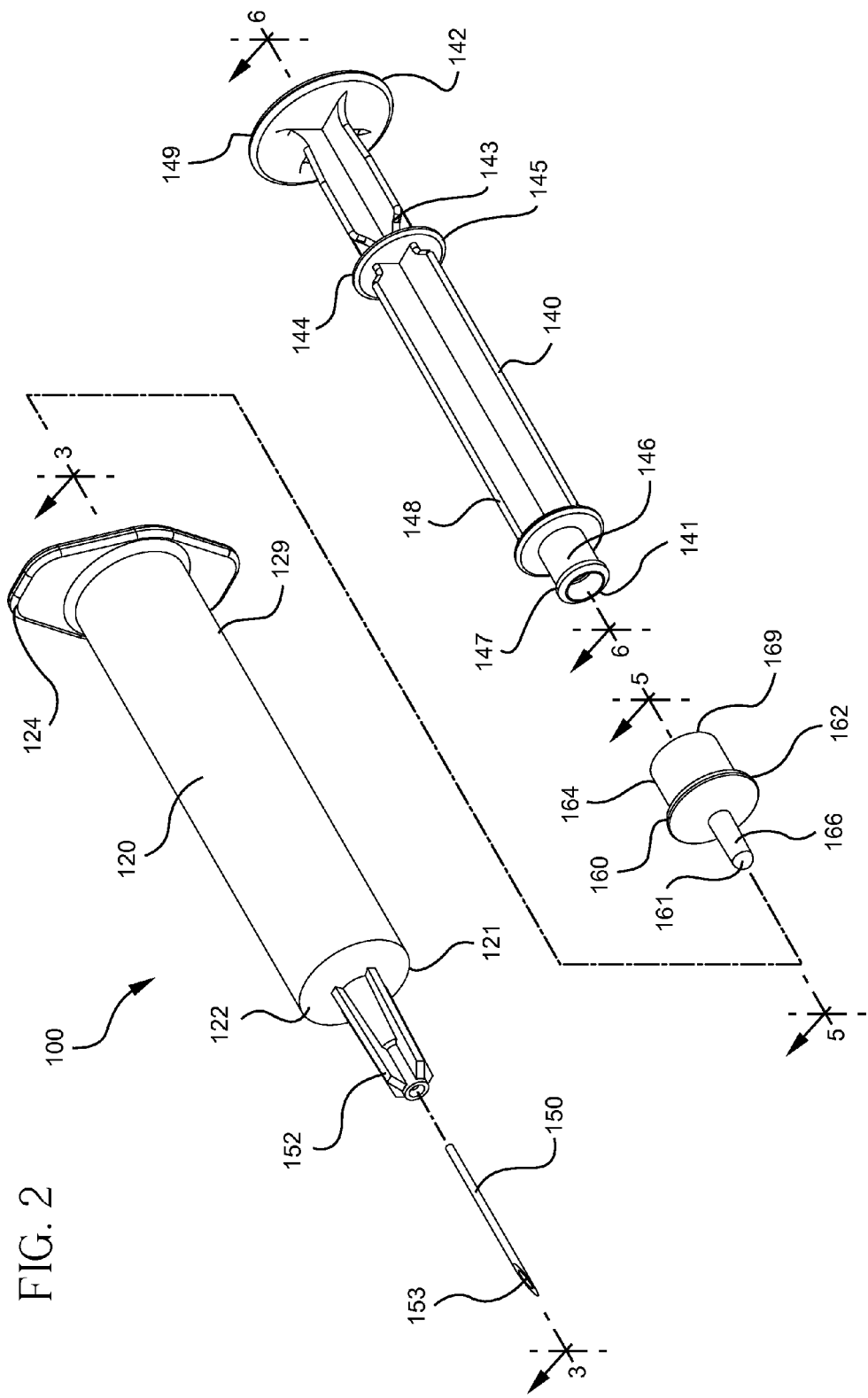
FIG. 2 illustrates a disassembled perspective view of a syringe assembly according to an embodiment of the invention.

FIG. 1 shows a syringe assembly 100 according to one or more embodiments. As shown in FIG. 2, the syringe assembly includes a barrel 120, a plunger rod 140 and a stopper 160, arranged such that the proximal end 169 of stopper is attached to the distal end 141 of the plunger rod. The connected stopper 160 and plunger rod 140 are inserted into the proximal end 129 of the barrel 120.

As best shown in the FIG. 3, the barrel 120 has a cylindrical sidewall 110 with an interior surface 126 that defines a chamber 128. In one embodiment, the chamber 128 holds the contents of the syringe assembly which may include medication in powdered or fluid form. The barrel 120 is shown as having an open proximal end 129, a distal end 121, and a distal wall 122. The distal wall 122 has an opening 111 in fluid communication with the chamber 128.

The sidewall 110 of the barrel 120 defines a chamber having a continuous inner diameter along the longitudinal axis of the syringe. Alternatively, the barrel can include a sidewall has an inner diameter, which decreases linearly from the proximal end to the distal end. It is to be understood that the configuration shown is merely exemplary, and the components can be different in shape and size than shown. For example, the barrel can have an exterior prism shape, while retaining a cylindrical interior shape. Alternatively, both the exterior and interior surfaces of the barrel can have non-circular cross-sectional shapes.

The syringe barrel 120 is shown as having a peripheral flange 124 attached at the proximal end 129 of the barrel 120. The barrel 120 further includes a needle cannula 150, having a lumen 153 attached to the opening 111 in the distal wall 122 of the barrel 120. As is known in the art, attachment means 152 is provided for attaching the needle cannula 150 to the distal wall 122. The assembly 100 may also include a protective cap over the needle cannula (not shown).

As shown more clearly in FIG. 4, the barrel 120 further includes a rib 123 adjacent its proximal end 129. The inner diameter of the barrel at the location of the rib 123 is smaller than the inner diameter of the barrel 120 at other locations along the length of the barrel. One or more optional tabs or detents can be used to create a region of the barrel having a diameter smaller than the inner diameter of the barrel 120. In a specific embodiment, the rib can include a ring formed along entire circumference of the interior surface 126 or a portion of the interior surface 126 of the inner diameter of the barrel 120 (not shown). The barrel 120 also includes a diameter transition region 127 adjacent to the rib 123 at the proximal end 129 (as shown in FIG. 3) of the barrel 120. The inner diameter of the barrel at the diameter transition region 127 increases from the distal end 121 to the proximal end 129 (as shown in FIG. 3) of the barrel 120. In the embodiment shown, the barrel includes an increased diameter region 125 adjacent to the diameter transition region at the proximal end 129 (as shown in FIG. 3) of the barrel. The inner diameter of the barrel 120 at the increased diameter region 125 is greater than the inner diameter of the barrel of the entire diameter transition region 127.

The barrel may be made of plastic, glass or other suitable material. The barrel further includes optional dosage measurement indicia (not shown).

Figure 5:
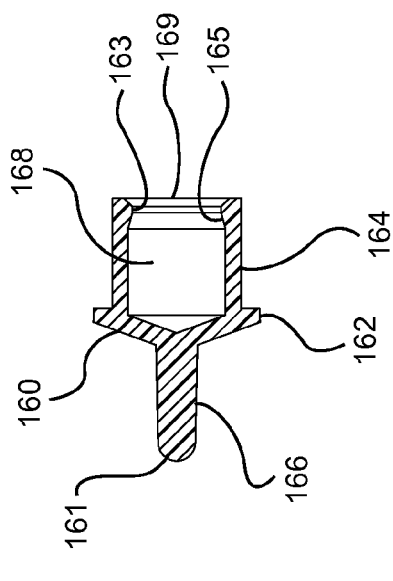
FIG. 5 is a cross-sectional view of the stopper shown in FIG. 2 taken along line 5-5.

Referring now to FIG. 5, the stopper 160 has a distal end 161, a proximal end 169, a stopper body 164 and a peripheral edge 162 which forms a seal with the interior surface 126 of the barrel. In one or more embodiments, the peripheral edge 162 of the stopper 160 has a larger diameter than the diameter of the interior surface of the rib 123. The stopper 160 shown in FIG. 5 includes an optional elongate tip 166 on its distal end 161 to facilitate reduction of the residual fluid and expulsion of fluid from the syringe barrel.

The stopper 160 is shown as further having a tapered portion 165 adjacent to the stopper body 164 at its proximal end 169. A neck 163 is adjacent to the tapered portion 165 at the proximal end 169 of the stopper 160. The stopper body 164 is shown as also including an interior recess 168, which allows the stopper-engaging portion 146 of the plunger rod 140 to connect to the stopper 160. A peripheral rim 147 may be provided to help retain the stopper 160 on the plunger rod 140. As with the rib of the barrel, detents or tabs can be used to retain the stopper 160 on the plunger rod 140.

The stopper is typically made of plastic or other easily disposable and/or recyclable material. It may be desirable to incorporate natural or synthetic rubber in the stopper or use a natural or synthetic rubber seal with the stopper. It will be understood that the stopper may incorporate multiple seals.

Figure 6:
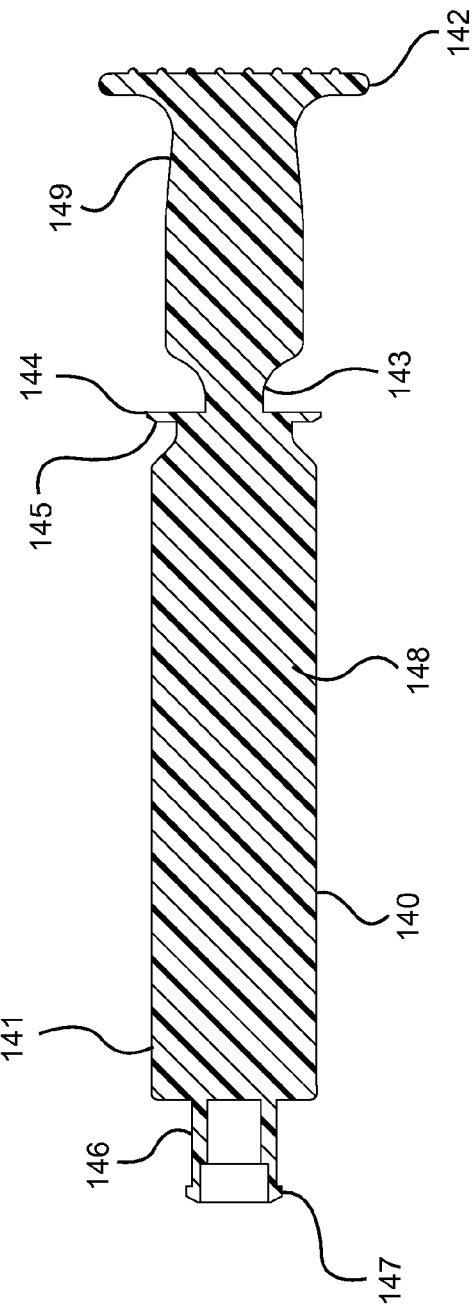
FIG. 6 is a cross-sectional view of the plunger rod shown in FIG. 2 taken along line 6-6.

Referring now to FIG. 6, the syringe assembly includes a plunger rod 140 having a proximal end 149, a distal end 141, and a main body 148 extending between the proximal end 149 and distal end 141. The plunger rod 140 further includes a thumb press 142 at the proximal end 149 of the plunger rod 140. In the embodiment shown, the thumb press 142 further includes a textured surface, writeable surface and/or label.

Figure 11:
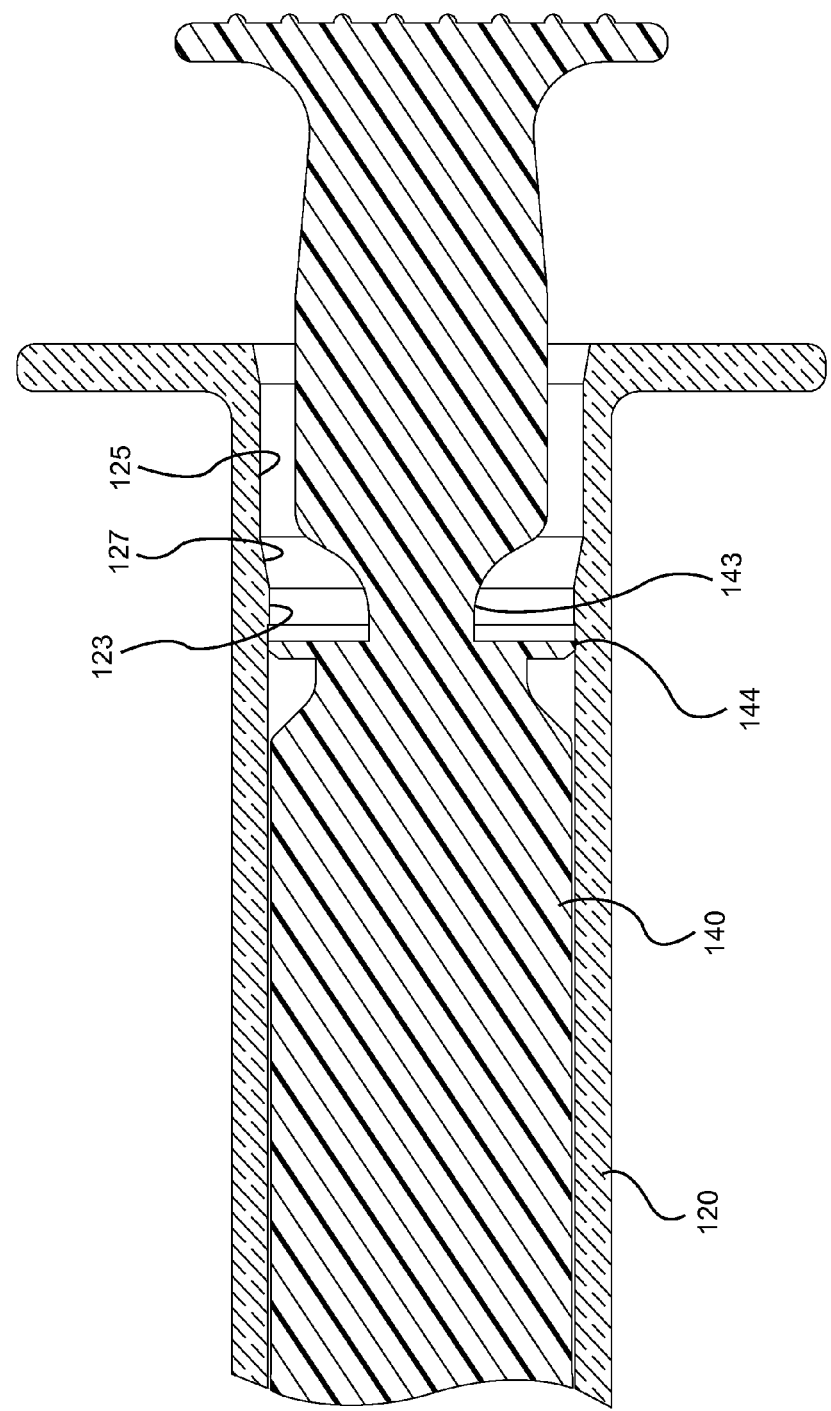
FIG. 11 is an enlarged view of a proximal portion of the assembly shown in FIG. 10.

Still referring to FIG. 6, the plunger rod 140 further includes a protrusion 144 shown as an annular protrusion 144 between the thumb press 142 and the main body 148. The outer diameter of the plunger rod at the protrusion 144 is greater than the inner diameter of the barrel 120 at the rib 123. In some embodiments of the invention, the protrusion 144 includes a tapered portion 145 that facilitates distal movement of the protrusion past the rib 123 and into the barrel 120, as will become apparent in the subsequent discussion of operation of the syringe. In at least one embodiment, the syringe assembly is configured to allow the protrusion 144 to advance distally past the rib 123, to lock the plunger rod in the barrel when the user bottoms out the plunger rod in the barrel (as more clearly shown in FIGS. 10-11). In certain embodiments, the plunger rod 140 further includes at least one frangible connection or point 143 for separating at least a portion of the plunger rod from the main body when a user applies sufficient proximal force to the plunger rod after it has been locked. In the embodiment shown, the frangible point 143 is located between the protrusion 144 and the thumb press 142. It will be understood that the frangible connection or point 143 shown is exemplary, and other suitable means for permanently damaging the plunger rod or otherwise separating at least a portion of the plunger rod from the main body may be provided.

In the embodiment shown, the stopper 160 is permitted to move distally and proximally within the barrel when connected to the stopper-engaging portion 146 of the plunger rod 140. As will be understood better with the description of operation of the syringe assembly and with reference to FIG. 7, the stopper is capable of moving distally and proximally a pre-selected axial distance 132 relative to the stopper-engaging portion.

In alternative embodiments, the stopper is fixed with respect to the plunger rod. In such embodiments, the axial distance may now be zero. It will be appreciated that in such embodiments, the syringe will be in an initial position, as supplied, where there is a gap between the stopper and the distal wall of the barrel. As the user fills the syringe, the stopper and the plunger rod move together in a proximal direction. As the user expels the contents of the syringe, the stopper and the plunger rod move together in the distal direction, the flexible protrusion is permitted to move past the locking rib.

The plunger rod may be made of plastic or other suitable material. The protrusion may also be comprised of plastic or a harder material suitable for locking the plunger rod within the barrel.

In FIG. 7, the barrel 120 holds the stopper 160 and plunger rod 140 in the chamber, wherein the stopper is bottomed, "parked" or is in contact with the distal wall 122 of the barrel 120. The peripheral edge of the stopper 162 forms a seal with the interior surface 126 of the barrel 120. In one embodiment, the stopper 160 is connected to the stopper-engaging portion 146 of the plunger rod 140. The stopper-engaging portion 146 is removeably held in the recess 168 of the stopper body 164 by the neck 163.

In FIG. 7, a gap between stopper 160 and the distal end of the main body 148 defines a pre-selected axial distance 132 prior to the injection cycle. In at least one embodiment, the protrusion 144 remains on the proximal side of the rib 123 because the length of the plunger rod 140 and stopper combined, along with the pre-selected axial distance 132, is greater than the length of the barrel 120 from the distal wall 122 to the proximal end of the barrel 120. The distance between the protrusion 144 and the peripheral edge 162 of the stopper body 164 defines a first distance, D1.

FIG. 8 illustrates the syringe assembly in use and specifically shows an aspiration or filling step, according to one or more embodiments of the present invention. When the user applies a force to the plunger rod 140 in the proximal direction shown by the arrow in FIG. 8, the plunger rod 140 and the stopper 160 move together in the proximal direction, while the stopper-engaging portion 146 is connected to the stopper 160 by the rim 147. In one or more embodiments, the gap defining the pre-selected axial distance 132 is maintained while the stopper 160 and plunger rod 140 move together in the proximal direction along the interior surface of the syringe barrel. The user terminates the application of proximal force on the plunger rod 140 once the desired amount of medicament is drawn into the syringe. During the aspiration step, the plunger rod and the stopper body move in the proximal direction together to draw medication into the syringe, while maintaining the first distance D1.

FIG. 9 also shows the syringe assembly in use and specifically demonstrates application of distal force to the plunger rod during injection. In one embodiment, when the user applies a force in the distal direction to the plunger rod 140 as indicated by the arrow, the plunger rod 140 moves in a distal direction for the length of the gap defining the pre-selected axial distance 132 in FIG. 7, while the stopper 160 remains stationary. The stopper 160 remains stationary because the frictional force created by the peripheral edge 162 of the stopper on the interior surface 126 of the barrel is greater than the frictional force created by the stopper-engaging portion 146 entering the recess 168 of the stopper 160. Consistent with at least one embodiment, once the stopper-engaging portion has distally moved the length of the pre-selected axial distance 132 and is in contact with the proximal end of the recess 169, the stopper 160 and the plunger rod 140 begin to move in tandem in the distal direction. Further, the force applied by the user is greater than the friction between the peripheral edge 162 of the stopper 160 and the interior surface 126 of the barrel, and therefore the stopper 160 is forced to move in the distal direction with the plunger rod 140. In one embodiment, the user may inject a limited amount of the fluid aspirated or exert a limited force on the plunger rod in the distal direction to flush or expel some of the aspirated fluid, without locking the plunger rod, provided that the syringe assembly is not bottomed. However, as will be described further with respect to FIG. 10, a user may bottom the stopper against the distal wall of the syringe barrel, locking the plunger rod in the barrel.

When expelling the contents of the syringe, the plunger rod moves in a distal direction the length of the pre-selected axial distance 132 shown in FIG. 7 while the stopper body remains stationary, consequently closing the gap defining the pre-selected axial distance 132. After the contents of the syringe have been fully expelled, the distance between the protrusion 144 and the peripheral edge 162 defines a second distance, D2, wherein D2 is the difference between the first distance, D1, and the gap defining a pre-selected axial distance 132.

FIG. 10 illustrates an embodiment of the syringe assembly after the plunger rod has been locked inside the barrel. In one or more embodiments, the entry of the stopper-engaging portion into the recess 168 of the stopper 160 (as also shown in FIG. 9) closes the gap defining the pre-selected axial distance 132, allowing the protrusion 144 to advance past the locking rib 123 (as more clearly shown in FIG. 11). The protrusion 144 has an outer diameter greater than the inner diameter of the barrel at the rib 123. Accordingly, in one or more embodiments, the rib 123 locks the protrusion 144 inside the barrel 120, and prevents proximal movement of the plunger rod 140.

Figure 12:
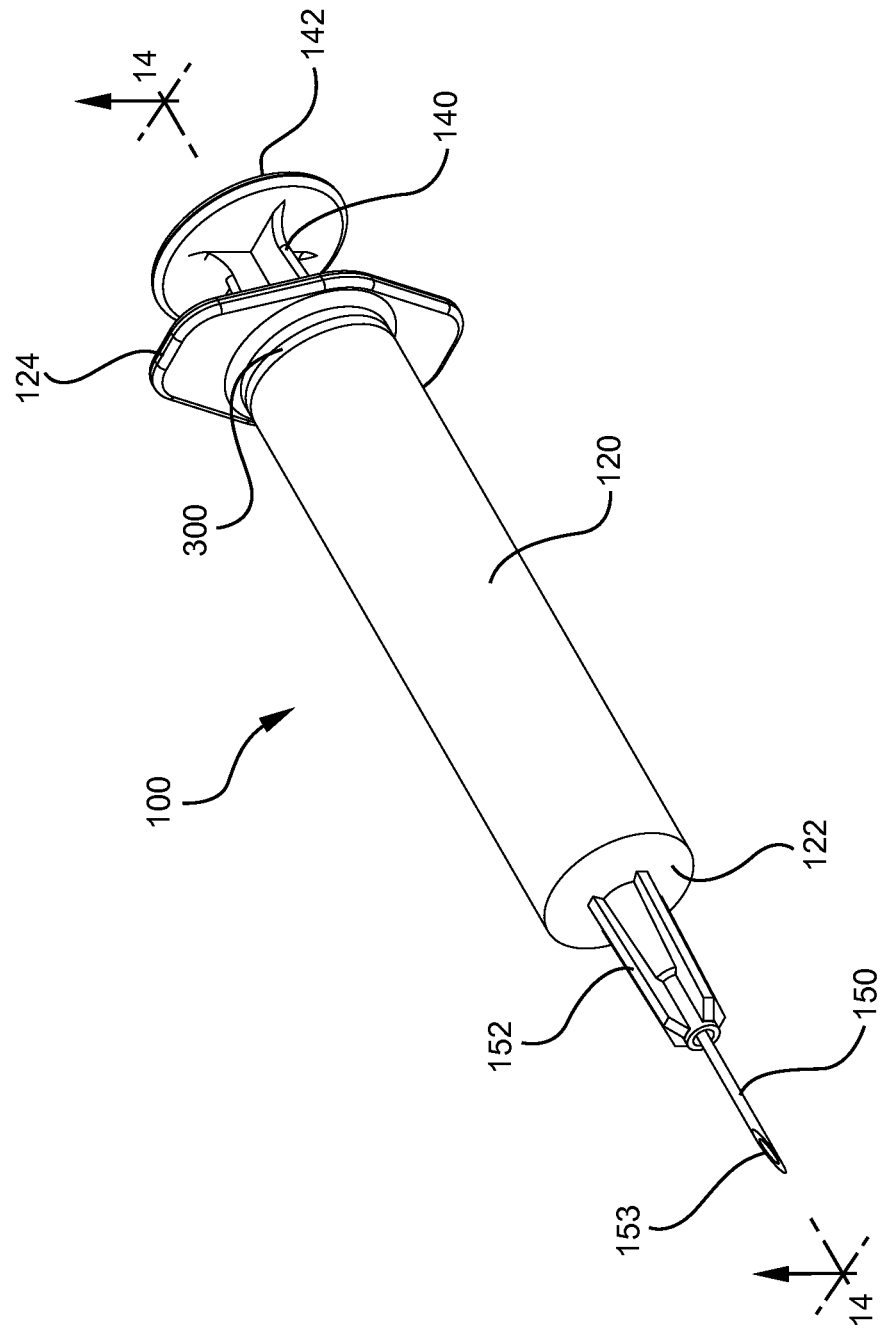
FIG. 12 illustrates a perspective view of an embodiment of a syringe assembly having a visual marker disposed on the barrel.

FIG. 12 shows a syringe assembly 100 in which the barrel 120 includes a visual marker 300. The marker is aligned with the rib 123, as more clearly shown in FIG. 16. The marker can be integrally formed on the sidewall of the barrel or can be added to the exterior surface of the sidewall. The marker can be printed in ink, adhesively applied, a textured surface or a separate piece that is fixed around the syringe barrel. The marker can form a ring around the circumference of the side wall or be in the form of tabs disposed at regular intervals around the circumference of the side wall. In a specific embodiment, the marker is a colored stripe. In a more specific embodiment, the marker can include text in the form of one or more letters and/or numbers, geometric shapes, symbols or combinations thereof to inform users the syringe is disabled.

Figure 13:
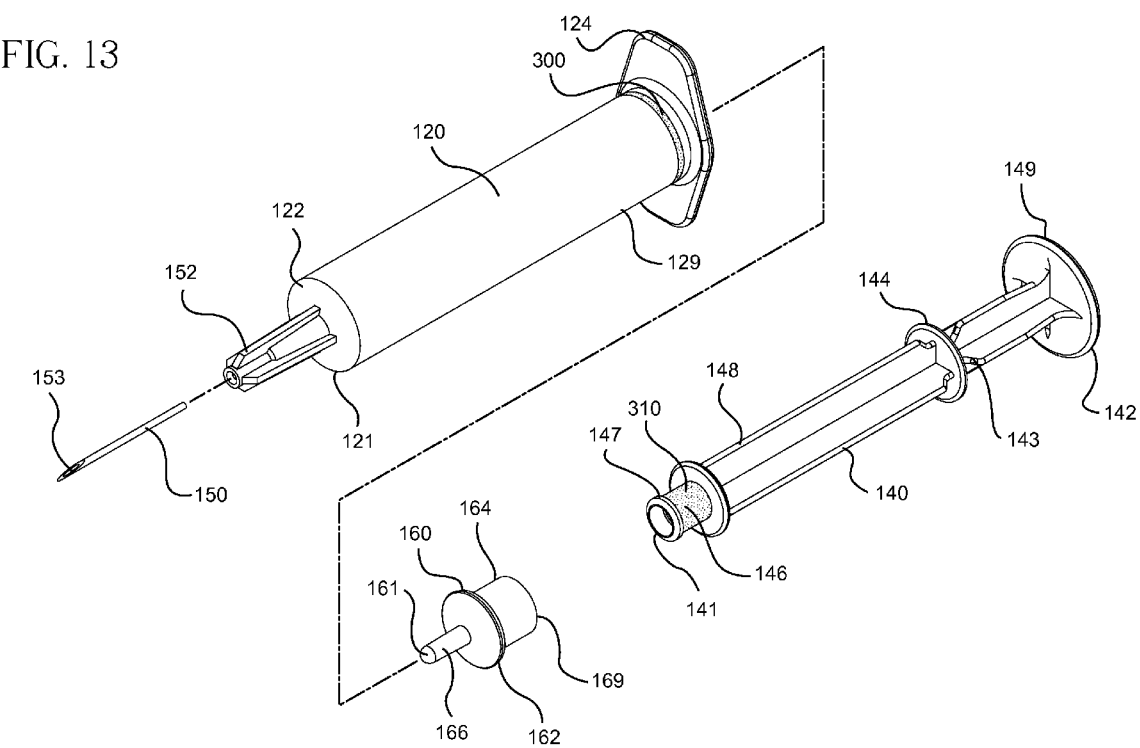
FIG. 13 illustrates a disassembled perspective view of an embodiment of a syringe assembly with visual indicators or markers disposed on the barrel and the stopper-engaging portion of the plunger rod.

FIG. 13 shows a plunger rod 140 having a visual indicator or display 310 disposed on the stopper-engaging portion 146. As with the visual marker 300, the visual indicator 310 can be integrally formed with the stopper-engaging portion of the plunger rod or be added to the exterior surface thereof. The indicator or display can be printed in ink, adhesively applied, a textured surface or a separate piece that is fixed to the stopper engaging portion. In one or more embodiments, the indicator or display can comprise a pattern, a solid portion and or can cover the entire surface of the stopper-engaging portion. In a specific embodiment, the indicator is a colored stripe disposed along the length of the stopper-engaging portion 146 between the distal end 141 and the main body 148 of the plunger rod. In a more specific embodiment, the indicator is a colored stripe disposed along the circumference of the stopper-engaging portion 146 of the plunger rod. In an even more specific embodiment, the marker can include text in the form of one or more letters and/or numbers, geometric shapes, symbols or combinations thereof.

As more clearly shown in FIG. 14 a gap between stopper 160 and the distal end of the main body 148 defines a pre-selected axial distance 132 prior to the injection cycle. The visual indicator 310 is visible when the gap is present. The visual marker 300 is disposed on the exterior surface of the barrel 120 and aligned with the rib 123. As described with reference to FIG. 8, when the user applies a force to the plunger rod 140 in the proximal direction shown by the arrow in FIG. 8, the plunger rod 140 and the stopper 160 move together in the proximal direction, while the stopper-engaging portion 146 is connected to the stopper 160 by the rim 147. In one or more embodiments, the gap defining the pre-selected axial distance 132 is maintained while the stopper 160 and plunger rod 140 move together in the proximal direction along the interior surface of the syringe barrel. Accordingly, the visual indicator 310 continues to be visible.

As described with reference to FIG. 9, when expelling the contents of the syringe, the plunger rod moves in a distal direction the length of the pre-selected axial distance 132 shown in FIGS. 7 and 14 while the stopper body remains stationary, consequently closing the gap defining the pre-selected axial distance 132. The movement of the stopper-engaging portion, in the distal direction relative to the stopper allows the stopper-engaging portion 146 of the plunger rod to move into the recess 168 of the stopper (as shown in FIG. 9). As can be more clearly seen in FIG. 15, this relative movement allows the stopper body 164 to cover the stopper-engaging portion and block visibility of the visual indicator 310.

Figure 16:
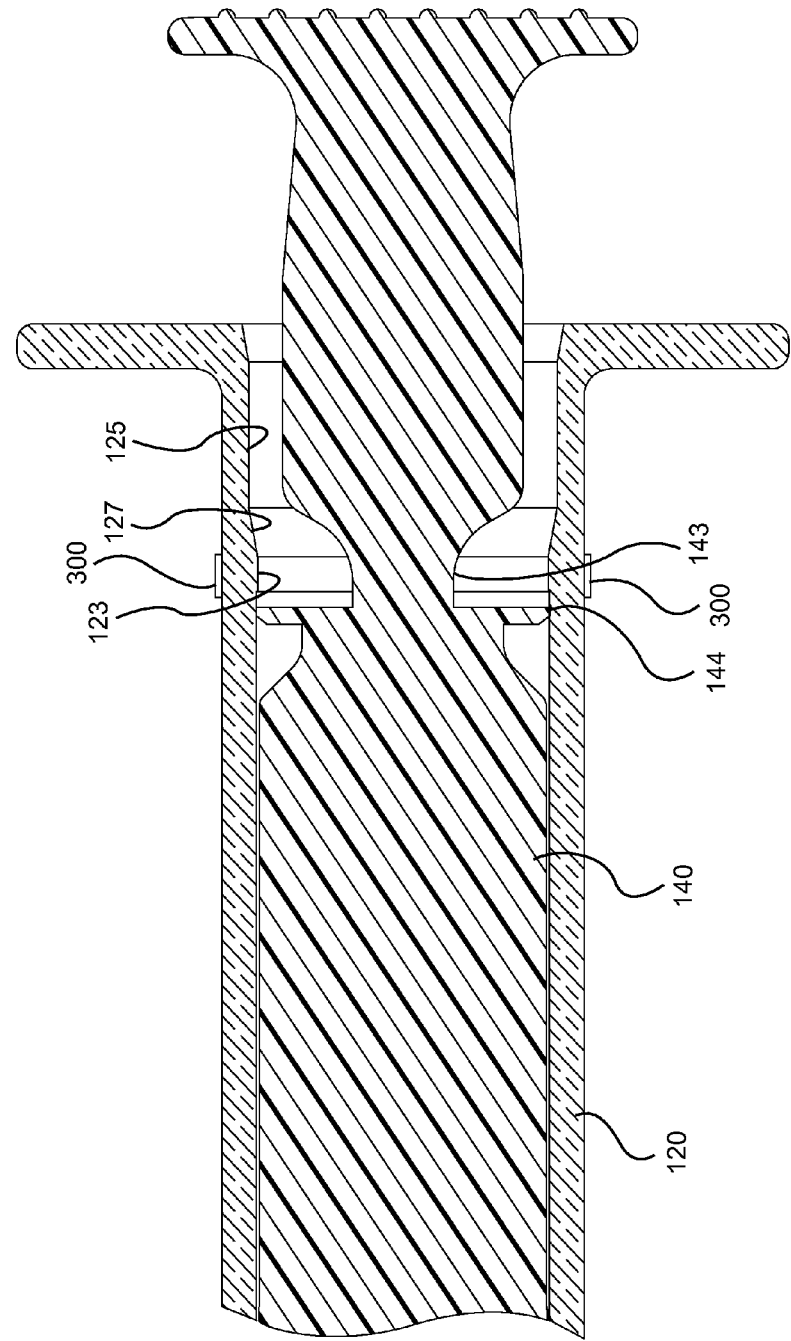
FIG. 16 is an enlarged view of a proximal portion of the assembly shown in FIG. 15.

As more clearly shown in FIGS. 15 and 16, the visual marker 300 disposed on the barrel 120 and aligned with the rib 123 also shows advancement of the protrusion 144 past the rib 123. In addition, the entry of the stopper-engaging portion into the recess 168 of the stopper 160 (as also shown in FIG. 9) also closes the gap defining the pre-selected axial distance 132, allowing the protrusion 144 to advance past the rib 123 (as more clearly shown in FIGS. 11 and 16). The location of the protrusion relative to the visual marker indicates whether the plunger rod has been locked within the barrel and the syringe assembly has been disabled. Before the plunger rod is locked, the protrusion 144 is proximally adjacent to the visual marker 300. Once the plunger rod is locked, the protrusion 144 is distally adjacent to the visual marker 300.

It will be appreciated that each of the visual marker 300 and the visual indicator 310 can be used alone or in combination.

Figure 17:
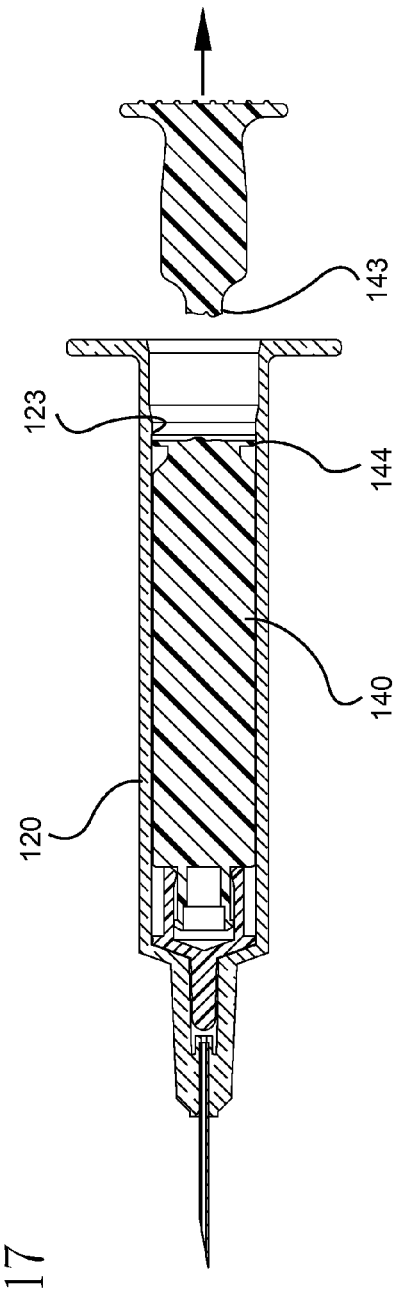
FIG. 17 is an illustration of FIG. 10 showing a proximal portion of the plunger rod being broken from the syringe assembly after the plunger rod has been locked in the syringe barrel.

FIG. 17 shows the assembly after the plunger rod 140 has been locked in the barrel 120. An attempt to reuse the syringe assembly by applying a force to the plunger rod 140 in the proximal direction causes a portion of the plunger rod 140 to separate at the frangible connection or point 143. The frangible connection or point 143 is designed so that the force holding exerted on the protrusion by the locking rib 123 while proximal force is being applied to the plunger rod 140 is greater than the force needed to break the plunger rod at the frangible point 143 and, therefore, the frangible point breaks or separates before the user is able to overcome the force exerted on the protrusion by the rib.

Figure 18:
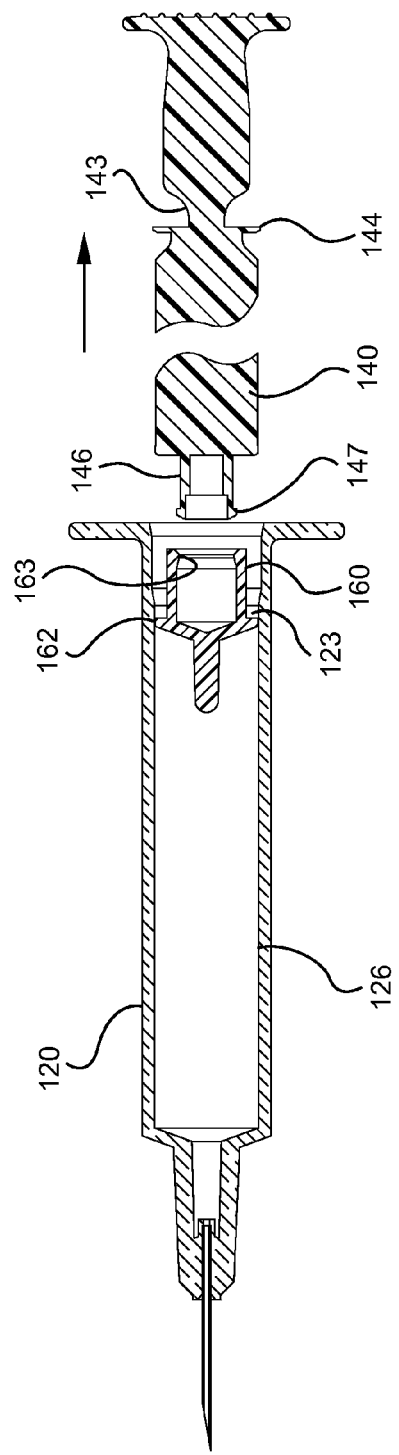
FIG. 18 is an illustration of FIG. 7 showing the plunger rod being moved in the proximal direction and the stopper disengaging from the plunger rod.

FIG. 18 shows the syringe assembly in a configuration in which the stopper 160 has separated from the stopper-engaging portion 146. According to one or more embodiments of the invention, the stopper 160 and stopper-engaging portion 146 disengage to prevent a user from disassembling the parts of the syringe assembly prior to use. As otherwise described in reference to FIG. 5, the peripheral edge 162 of the stopper 160 has a diameter greater than the diameter of the interior surface of the rib 123. Consistent with at least one embodiment of the invention, when a user applies a force to the plunger rod 140 in the proximal direction, the rib 123 locks the peripheral edge 162 of the stopper 160, and the rim 147 of the stopper-engaging portion 146 disconnects from the neck 163 of the stopper. The rib 123 exerts a greater force on the peripheral edge of the stopper than the force or friction exerted by the rim of the stopper-engaging portion of the plunger rod and neck portion of the stopper while proximal force is applied to the plunger rod.

Figure 19:
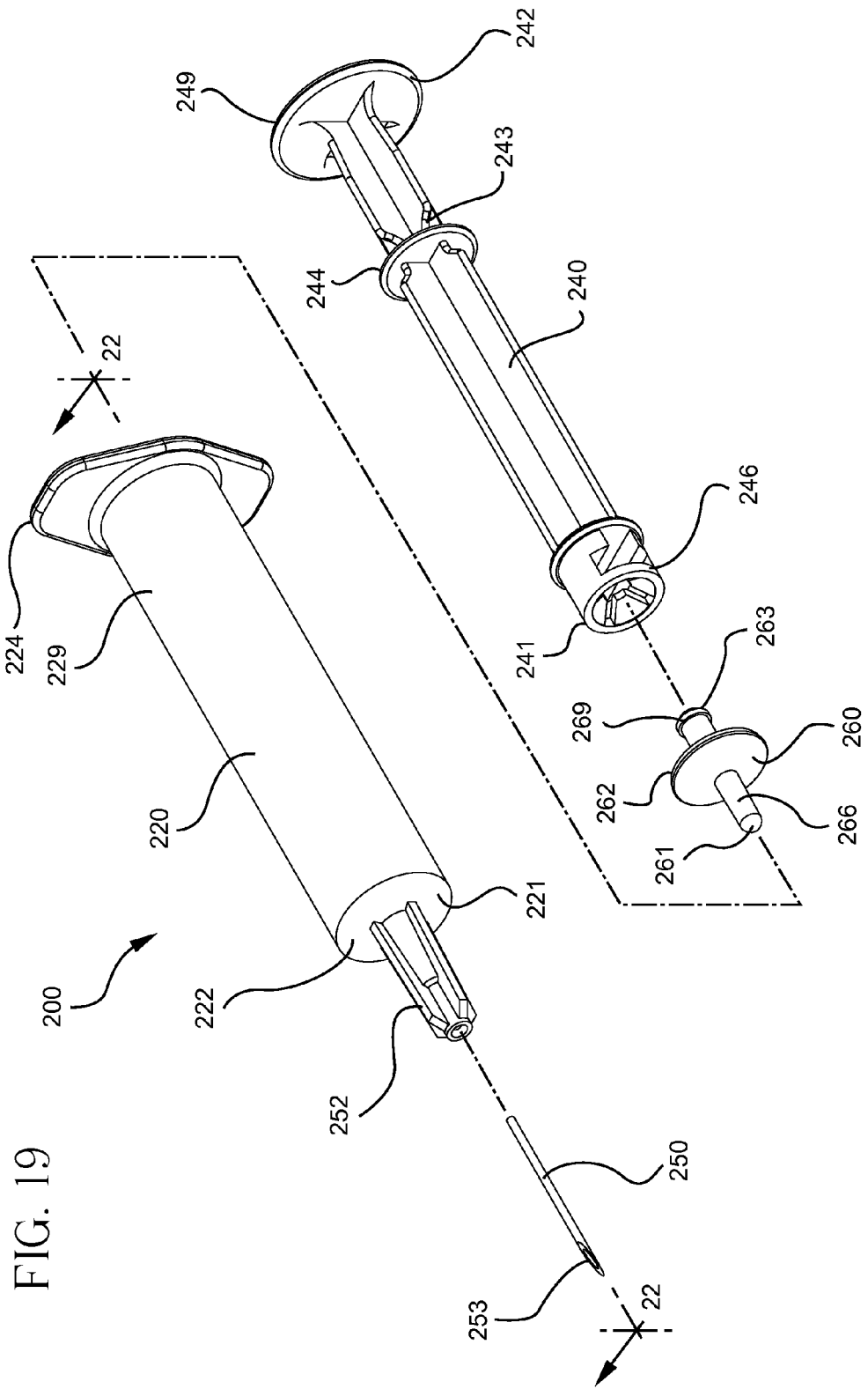
FIG. 19 a disassembled perspective view of a syringe assembly according to another embodiment of the invention.

FIG. 19 shows an example of a syringe assembly 200 according to another embodiment of the present invention. In the embodiment shown in FIG. 19, the assembly includes a barrel 220, a plunger rod 240 and a stopper 260, arranged so that the proximal end of stopper 269 is attached to the distal end of the plunger rod 241. The stopper 260 then plunger rod 240 is inserted into the proximal end of the barrel 229. A flange 224 is attached at the proximal end 229 of the barrel 220. The barrel 220 further includes a needle cannula 250 having a lumen 253, attached to the opening in the distal wall 222 at the distal end 221 of the barrel 220. One or more embodiments also include an attachment hub 252 for attaching the needle cannula 250 to the distal wall 222. The assembly may also include a protective cap over the needle cannula (not shown).

Figure 22:
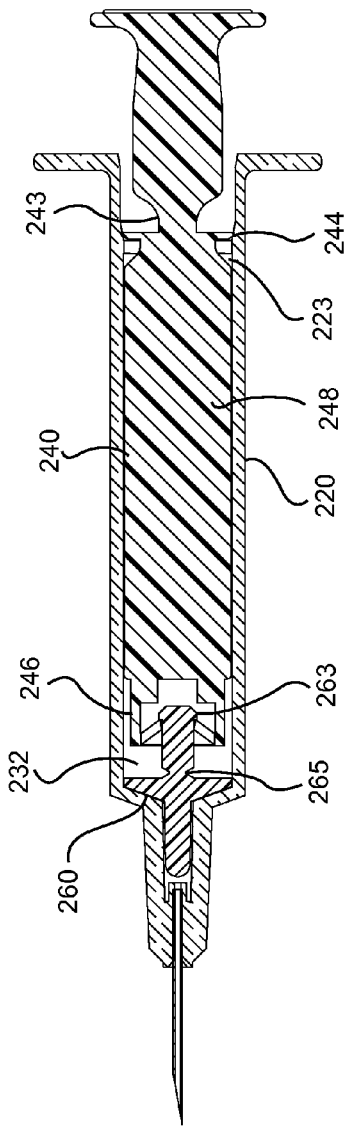
FIG. 22 is a cross-sectional view taken along line 22-22 of the syringe assembly shown in FIG. 19.

Similar to the barrel illustrated previously in FIGS. 3 and 4, and as shown in FIG. 22, the barrel further include a rib 223, locking rib or other means for locking the plunger rod within the barrel, having an interior surface with a smaller diameter than the diameter of the interior surface of the barrel.

Figure 20:
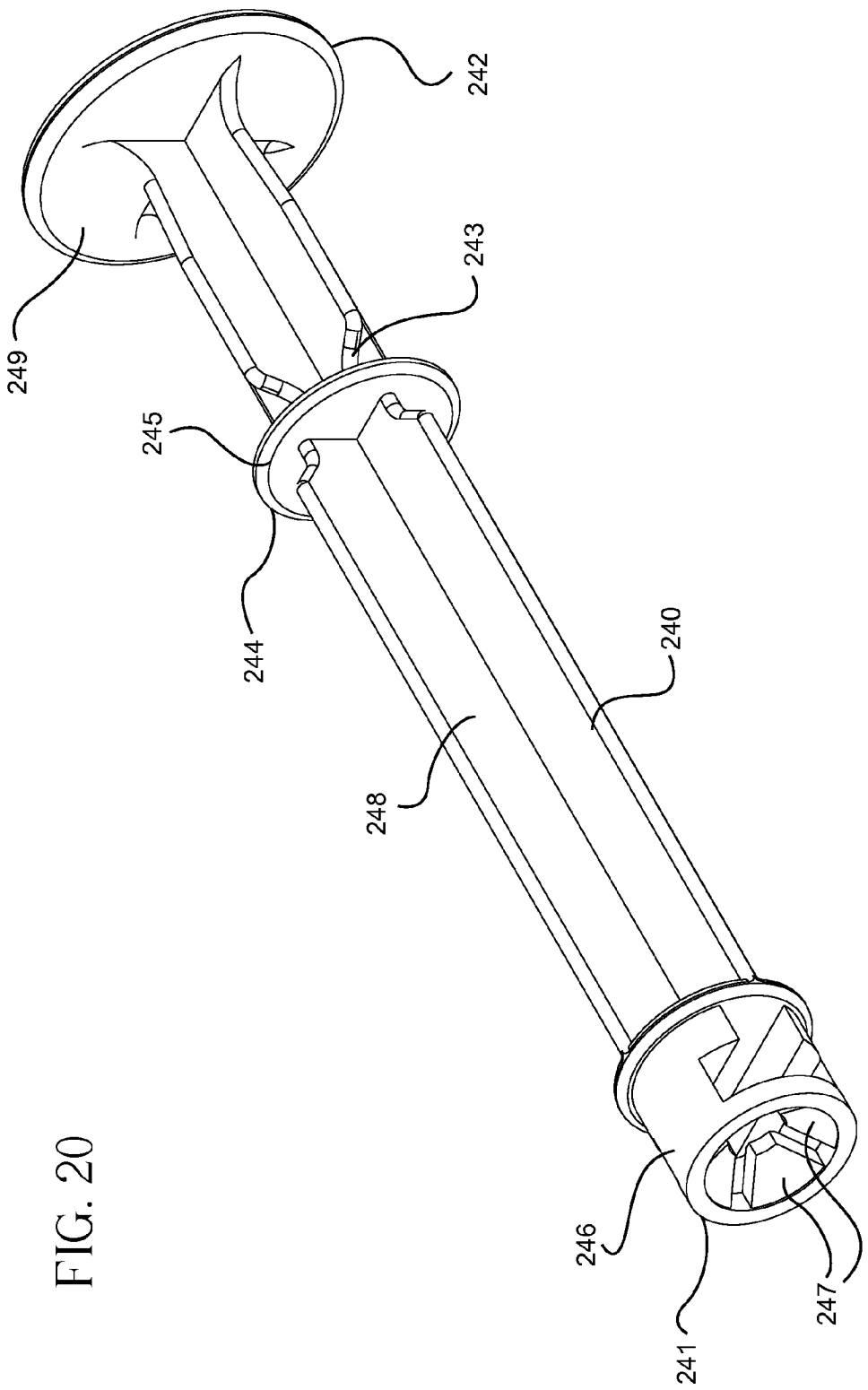
FIG. 20 is a perspective view of the plunger rod shown in FIG. 19.

Referring now to FIG. 20, a perspective view of a plunger rod 240 is shown as having a main body 248, a distal end 241 and a proximal end 249. The plunger rod 240 further includes a thumb press 242 at its proximal end and a stopper-engaging portion 246 at its distal end. Plunger rod 240 also includes a protrusion in the form of an annular protrusion 244 between the thumb press 242 and the main body 248. The protrusion 244 may include a tapered portion 245 to facilitate distal movement of the protrusion 244 past the rib 223 into the barrel 220. In some embodiments, the protrusion 244 has an outer diameter greater than the inner diameter of the barrel at the rib 223. In at least one embodiment, the configuration of the syringe assembly allows for the protrusion 244 to advance distally past the rib 223, to lock the plunger rod 240 in the barrel 220, when the user bottoms the syringe assembly (as more clearly shown in FIGS. 25-26 and discussed further below).

The plunger rod 240 shown further includes at least one frangible point 243. In the embodiment shown, the frangible point 243 of the plunger rod 240 is located between the protrusion 244 and the thumb press 242, but the frangible point could be in another location. A stopper-engaging portion 246 is included on the distal end 241 of the plunger rod 240. As shown, the stopper-engaging portion 246 also includes a plunger recess and a retainer 247. At least one embodiment of the invention includes a press-fit attachment or other suitable means for retaining the end of the stopper.

Figure 21:
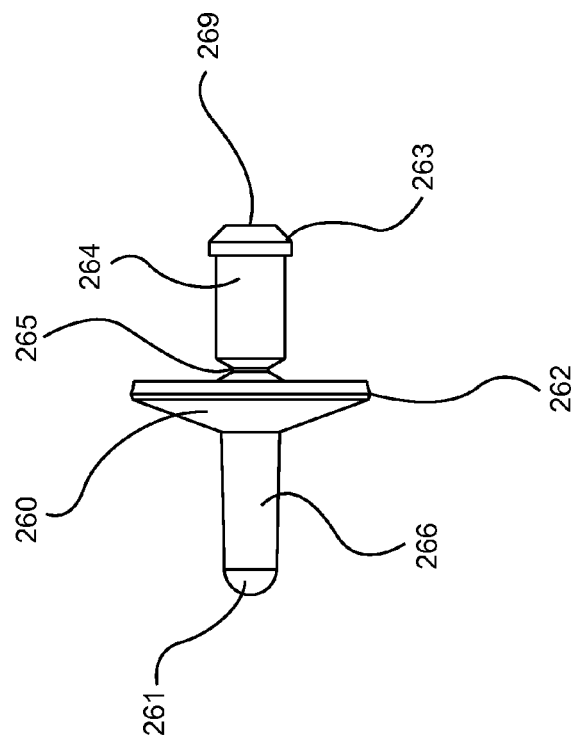
FIG. 21 is a side elevational view of the stopper shown in FIG. 19.

Referring now to FIG. 21, which shows an embodiment of the stopper 260 having a distal end 261 and a proximal end 269. According to at least one embodiment, the stopper 260 includes a peripheral edge 262 which forms a seal with the interior wall of the barrel 220 and has a diameter greater than the diameter of the interior surface of the barrel at the location of the rib 223 (as more clearly shown in FIGS. 22-24). As shown, an elongate tip 266 is provided at the distal end 261 of the stopper 260 to help expel the entire contents of the syringe. The stopper 220 can further include a stopper body 264 having a peripheral lip 263 at its proximal end 269, according to at least one embodiment of the invention. Further, the stopper 260 can include a stopper frangible connection 265 connecting the stopper body 264 to the stopper 260.

In this configuration, the stopper 260 and plunger rod 240 occupy the chamber of the barrel 220 and the stopper is bottomed against the distal wall of the barrel. Further, the peripheral edge 262 of the stopper 260 forms a seal with the interior surface of the barrel 220. The stopper 260 is connected to the stopper-engaging portion 246 of the plunger rod 240. As shown, the retainer 247 of the stopper-engaging portion 246 retains the peripheral lip 263 of the stopper 260.

Embodiments of the syringe assembly of FIGS. 19-27 can also include a visual marker 300, visual indicator 310 or both, as described with reference to FIGS. 13-16. In a specific embodiment, the barrel 220 of one or more embodiments can also include a visual marker aligned with the locking rib 223. In a more specific embodiment, the syringe assembly can include a visual indicator disposed on the stopper body 264.

According to one or more embodiments, there is a gap between the stopper 260 and the distal end of the main body 248 defining a pre-selected axial distance 232. In one or more embodiments, the distance between the protrusion 244 and the peripheral edge 262 of the stopper 260 defines a first distance, D1.

Figure 23:
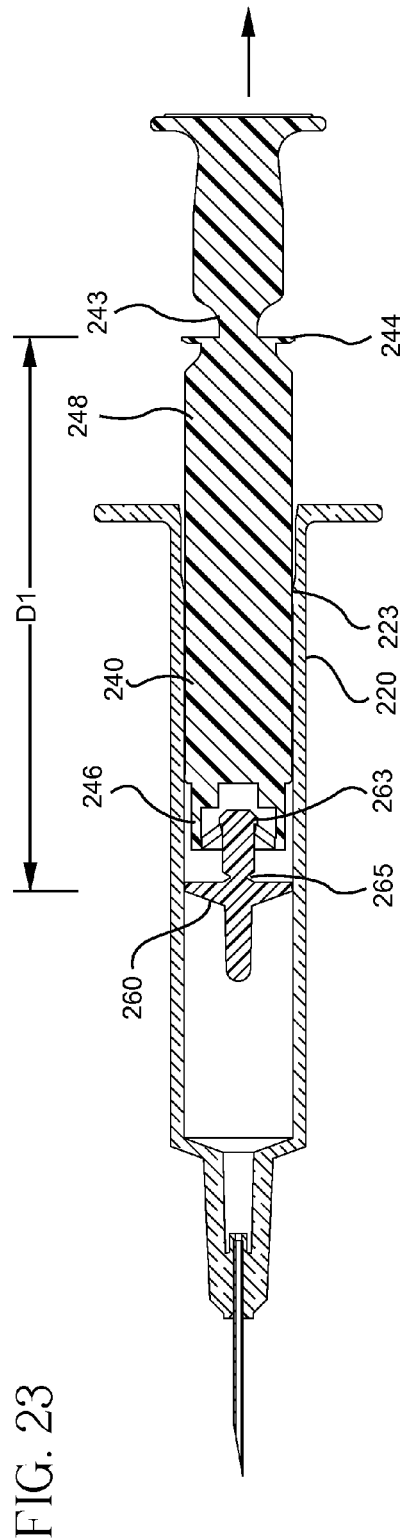
FIG. 23 is an illustration of FIG. 22 showing the plunger rod being moved in the proximal direction.

FIG. 23 illustrates the syringe assembly in use and specifically shows movement of the plunger rod during an aspiration or filling step according to one or more embodiments of the present invention. When the user applies a force to the plunger rod in the proximal direction, the plunger rod 240 and the stopper 260 move together in the proximal direction as indicated by the arrow, while the stopper-engaging portion 246 is connected to the stopper 260 by the rim 263. In this configuration, the gap defining the pre-selected axial distance 232 is maintained while the stopper 260 and plunger rod 240 move together in the proximal direction. The user applies proximal force to the plunger rod until a predetermined or desired amount of medicament is aspirated or drawn into the syringe. During the aspiration step, the plunger rod and the stopper body move in the proximal direction together to draw medication into the syringe, while maintaining the first distance D1.

Figure 24:
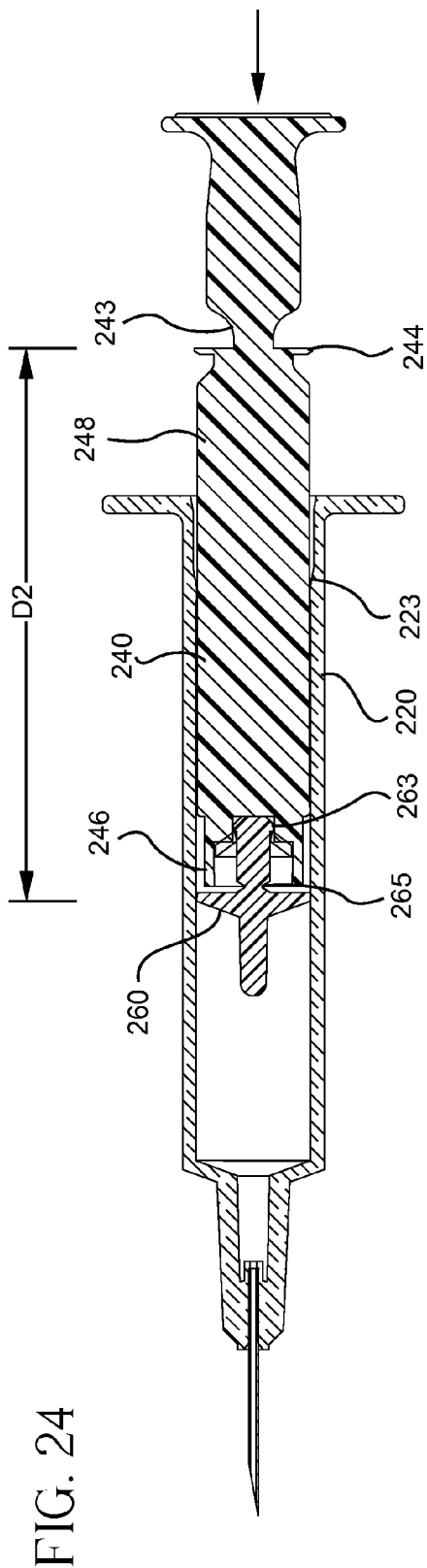
FIG. 24 is an illustration of FIG. 23 showing the plunger rod being moved in the distal direction.

FIG. 24 also shows the syringe assembly when distal force is applied to the plunger rod during an injection step according to at least one embodiment of the present invention. Application of a force in the distal direction closing the gap and moving the pre-selected axial distance 232 shown in FIG. 22, while the stopper 260 remains stationary. Consistent with at least one embodiment, once the stopper-engaging portion 246 has distally moved the pre-selected axial distance 232 and is in contact with stopper frangible connection 265, the stopper 260 and the plunger rod 240 begin to move in tandem in the distal direction.

When expelling the contents of the syringe, the plunger rod moves in a distal direction the length of the pre-selected axial distance 232 while the stopper body remains stationary. During and after the contents of the syringe have begun to be or have been fully expelled, the distance between the protrusion 244 and the peripheral edge 262 defines a second distance, D2, wherein D2 is the difference between the first distance, D1, and the gap defining a pre-selected axial distance 232.

In one embodiment, the user may inject a limited amount of the fluid aspirated or exert a limited force on the plunger rod in the distal direction to flush or expel some of the aspirated fluid, without locking the plunger rod, provided that the syringe assembly is not bottomed. However, as will be described further below, a user will typically expel substantially all of the contents of the syringe by bottoming the stopper on the distal wall of the barrel.

Figure 25:
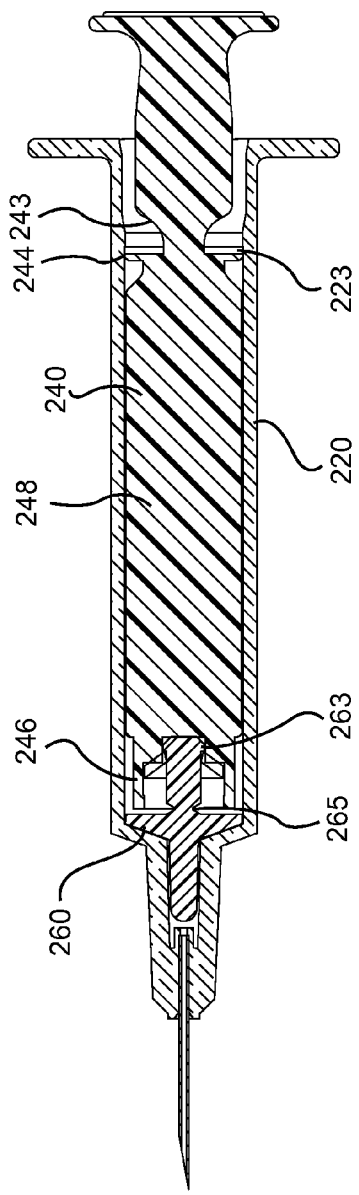
FIG. 25 is an illustration of FIG. 24 showing the plunger rod in a locked position in the syringe barrel.
Figure 26:
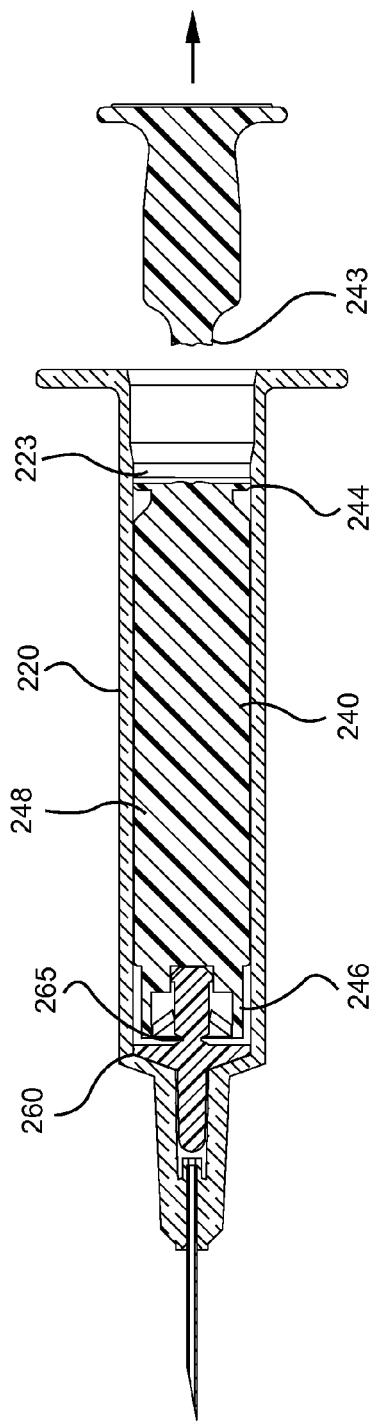
FIG. 26 is an illustration of FIG. 25 showing a proximal portion of the plunger rod being broken from the syringe assembly after the plunger rod has been locked in the barrel.

Referring now to FIG. 25, which illustrates the syringe assembly after the plunger rod 240 has been locked inside the barrel 220, the distal movement of the stopper-engaging portion 246 to the stopper frangible connection 265 of the stopper 260 (as also shown in FIG. 24) closes the gap defining the pre-selected axial distance and allows the protrusion 244 to advance past the rib 223, thereby locking the plunger rod 240 inside the barrel 220, preventing re-use of the syringe assembly Referring now to FIG. 26, the syringe assembly is shown in a configuration in which a user attempts to reuse the syringe assembly after the plunger rod 240 is locked inside the barrel 220 by applying a force to the plunger rod 240 in the proximal direction. Application of sufficient proximal force to the plunger rod causing a portion of the plunger rod 240 to separate at the frangible connection or point 243, as the holding force of the protrusion 244 and the rib exceeds the breaking force of the frangible point or connection.

Figure 27:
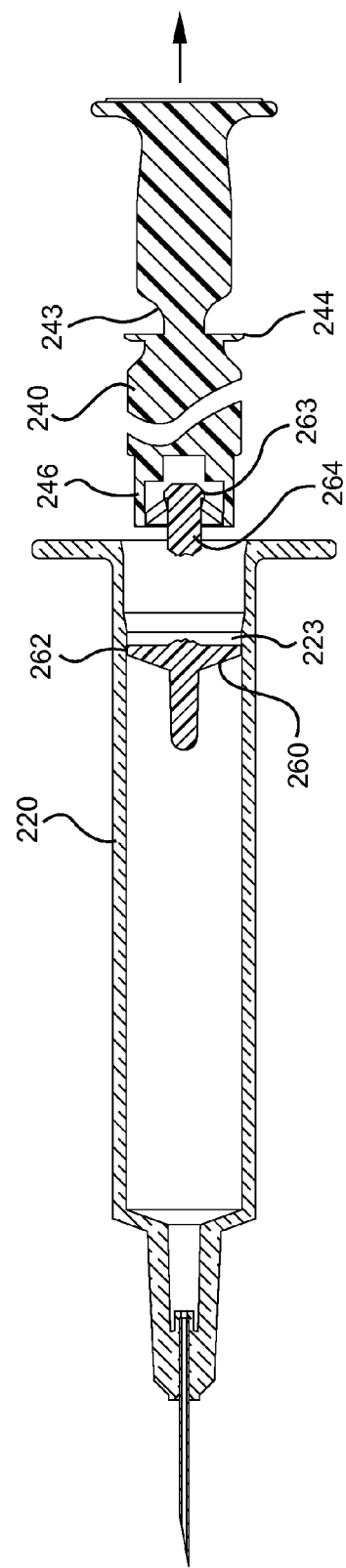
FIG. 27 is an illustration of FIG. 22 showing the plunger rod being moved in the proximal direction and the stopper disengaging from the plunger rod.

FIG. 27 shows the syringe assembly in a configuration after which proximal force has been applied to the plunger rod and the stopper has moved to the proximal end of the barrel. As shown in FIG. 27, the stopper 260 has separated from the stopper-engaging portion 246 of the plunger rod. The stopper frangible connection 265 breaks to prevent a user from disassembling the parts of the syringe assembly. As otherwise described herein, the peripheral edge of the stopper 260 has an outer diameter greater than the inner diameter of the interior surface of the barrel at the location of the rib 223. Consistent with at least one embodiment of the invention, when a user applies a force to the plunger rod 240 in the proximal direction, the rib 223 of the barrel 220 locks the peripheral edge 262 of the stopper 260, and the stopper frangible connection 265 breaks, separating the stopper body 264 from the stopper 260. Without being limited by theory, it is believed that the force required to break the stopper frangible connection is less than the force exerted on the peripheral edge of the stopper.

Figure 28:
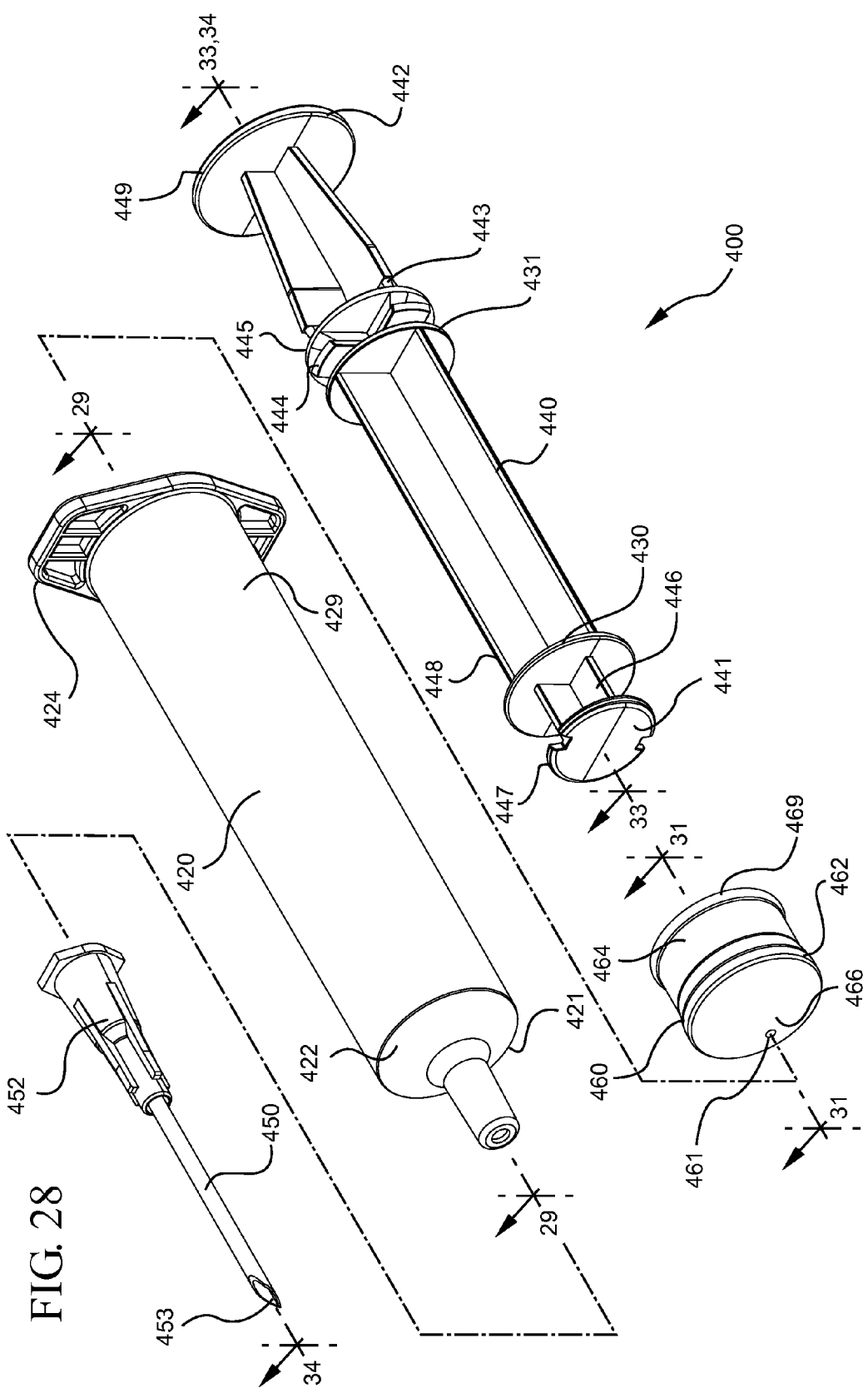
FIG. 28 shows a disassembled perspective view of a syringe assembly according to another embodiment of the invention.

FIG. 28 shows an example of a syringe assembly 400 according to another embodiment of the present invention. In the embodiment shown in FIG. 28, the assembly includes a barrel 420, a plunger rod 440 and a stopper 460, arranged so that the proximal end of stopper 469 is attached to the distal end of the plunger rod 441. The stopper 460 then plunger rod 440 is inserted into the proximal end of the barrel 429. The barrel includes a flange 424 attached at the proximal end 429 of the barrel 420 and a needle cannula 450 having a lumen 453 attached to the opening in the distal wall 422 at the distal end 421 of the barrel 420. One or more embodiments also include an attachment hub 452 for attaching the needle cannula 450 to the distal wall 442.

Figures 29, 30:
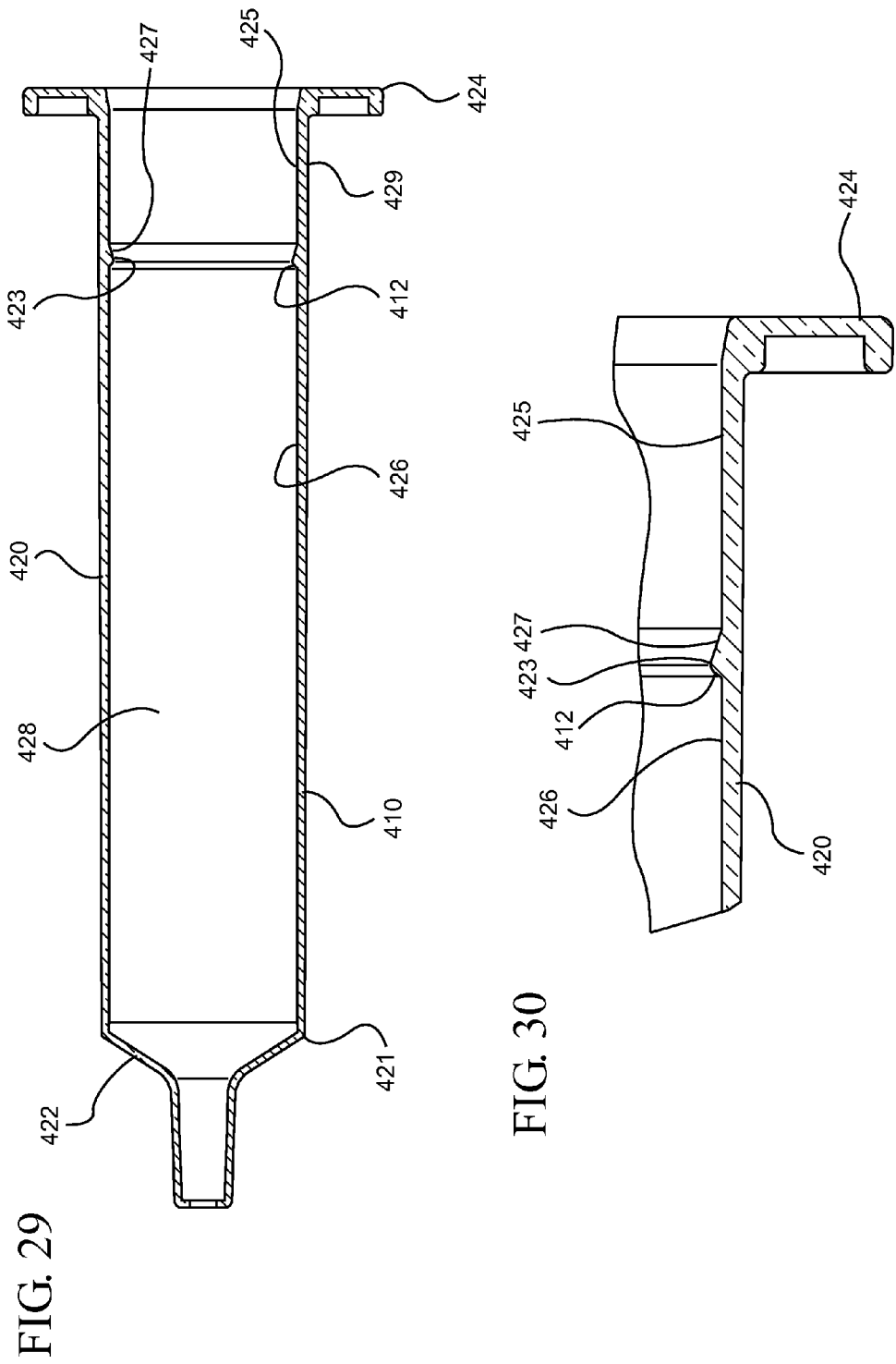
FIG. 29 shows a cross-sectional view of the barrel shown in FIG. 28 taken along line 29-29.
FIG. 30 is an enlarged view of a portion of the barrel shown in FIG. 29.

The barrel as shown more clearly in FIG. 29 further includes a cylindrical sidewall 410 with an inside surface 426 defining a chamber 428. As more clearly shown in FIG. 30, the barrel further includes a rib 423, locking rib or other means for locking the plunger rod within the barrel, having an interior surface with a smaller diameter than the diameter of the interior surface of the barrel. The distal end of the rib 423 further includes a distal portion 412 facing the distal end of the barrel 421. It will be understood that the rib 423 and the distal portion of the rib 412 can have different shapes and configurations. A ramp 427 is disposed proximally adjacent to the rib 423 having an increasing diameter from the rib to the open proximal end. An increased diameter region 425 is disposed proximally adjacent to the ramp 427. The increased diameter region 425 may have the same or larger diameter than the inside surface of the barrel 426.

Figure 31:
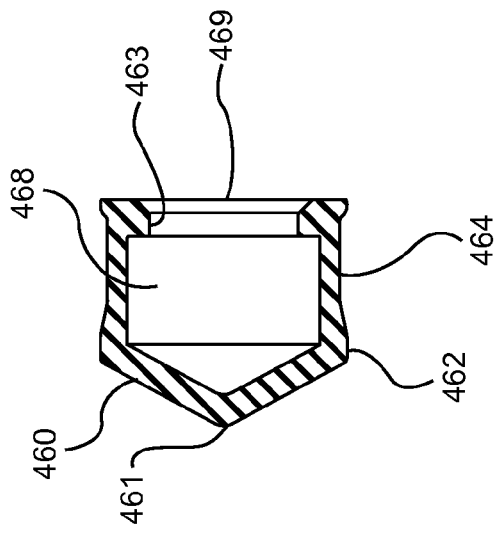
FIG. 31 is a cross-sectional view of the stopper shown in FIG. 28 taken along line 31-31.

Referring now to FIG. 31, which shows an embodiment of the stopper 460 having a distal end 461 and a proximal end 469. According to at least one embodiment, the stopper 460 includes a sealing edge 462 which forms a seal with the inside surface of the barrel 426 and has a diameter greater than the diameter of the inside surface of the barrel at the location of the rib 423 (as more clearly shown in FIGS. 29 and 30). The stopper 460 can further include a stopper body 464 defining an interior recess 468 and a neck 463 disposed at its proximal end 469, according to at least one embodiment of the invention. According to one or more embodiments, the stopper may be formed from an elastomeric or plastic material. The stopper may also be formed from other known materials in the art.

Figure 32:
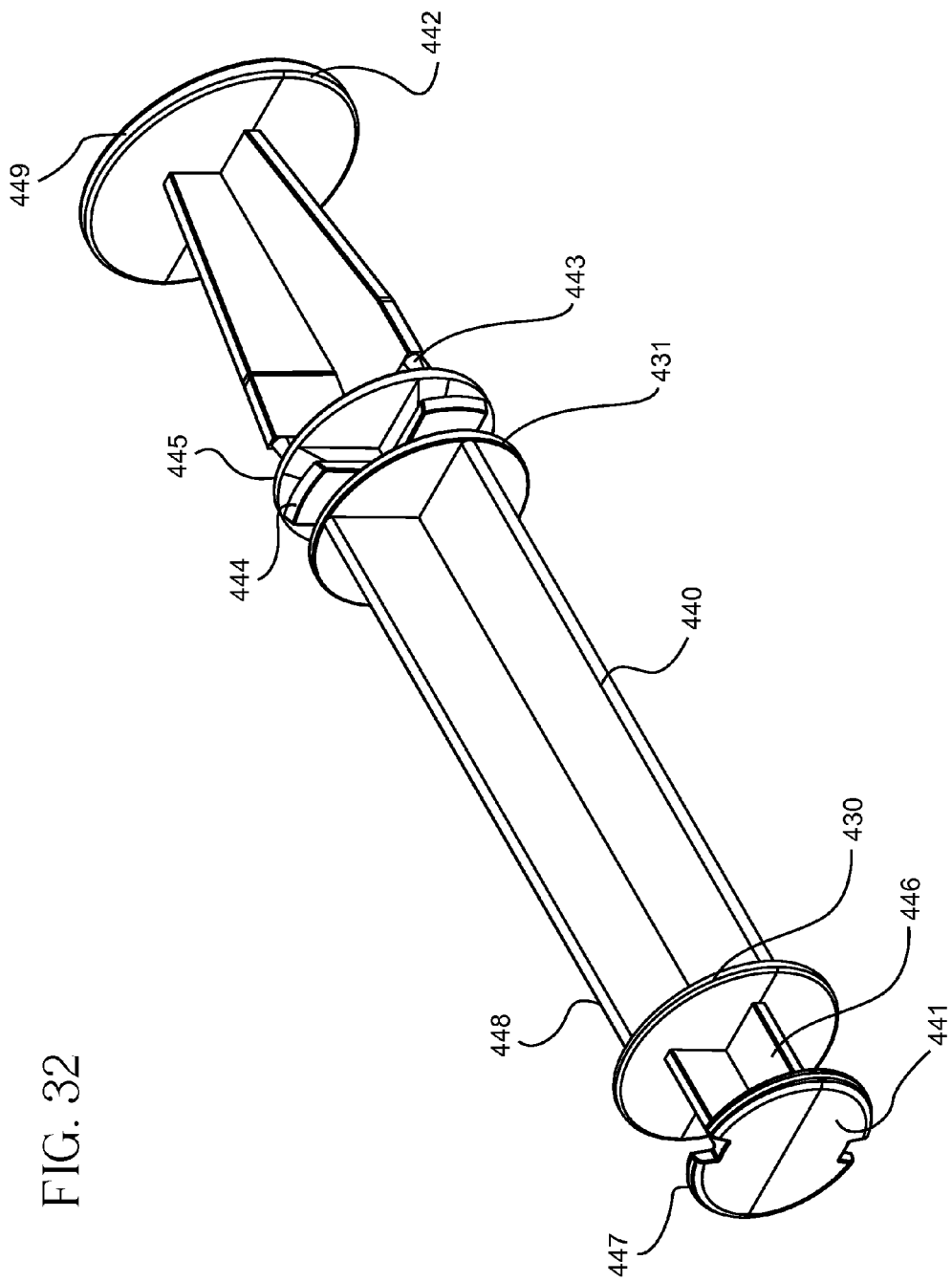
FIG. 32 illustrates a perspective view of the plunger rod shown in FIG. 28.

Referring now to FIG. 32, a perspective view of a plunger rod 440 is shown as having a main body 448, a distal end 441 and a proximal end 449. The plunger rod 440 further includes a thumb press 442 at its proximal end and a stopper-engaging portion 446 at its distal end. Plunger rod 440 also includes a flexible protrusion 444 between the thumb press 442 and the main body 448 and a support 445 proximally adjacent to the flexible protrusion, which provides additional stability to the plunger use and syringe 400 during use. In some embodiments, the flexible protrusion 444 has an outer diameter greater than the inner diameter of the barrel at the rib 423. In at least one embodiment, the configuration of the syringe assembly allows for the flexible protrusion 444 to advance distally past the rib 423, to lock the plunger rod 440 in the barrel 420, when the user bottoms the syringe assembly (as more clearly shown in FIGS. 37-38 and discussed further below). The plunger rod may further include an optional pair of discs 430, 431 disposed on the distal end and proximal end of the main body 448. The discs 430, 431 provide additional stability and may have alternate shapes, depending on the shape of the barrel.

Figure 33:
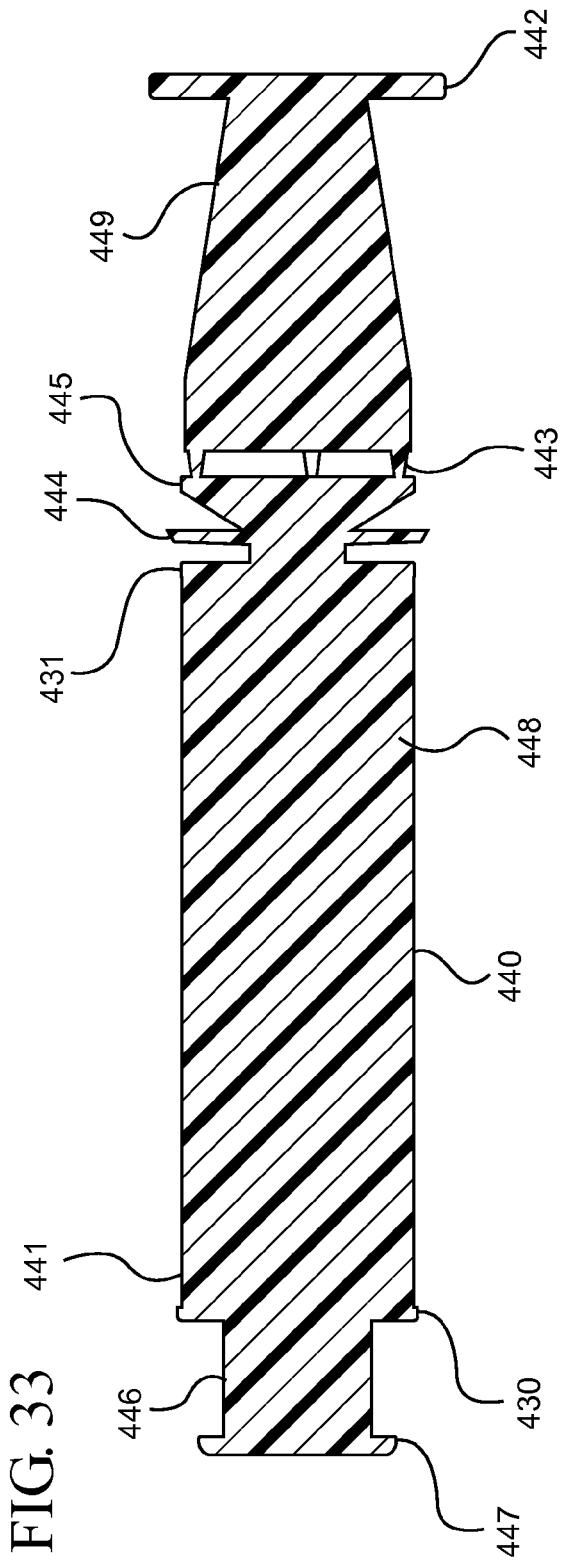
FIG. 33 is a cross sectional view of the plunger rod shown in FIG. 28 taken along lines 33-33.

As shown in FIG. 33, the plunger rod 440 further includes a plurality of frangible connections or bridges 443 adjacent to the support 445. In the embodiment shown, the plurality of frangible connections 443 of the plunger rod 440 is located between the support 445 and the thumb press 442, but the frangible connections could be in another location.

The distal end of the plunger rod 441 further includes a stopper-engaging portion 446. As shown, the stopper-engaging portion 446 also includes a retaining ring 447 for retaining the neck 463 of the stopper 460. At least one embodiment of the invention includes a press-fit attachment or other suitable means for retaining the end of the stopper.

When assembled, the stopper 460 is connected to the stopper-engaging portion 446 of the plunger rod 440. In the embodiment shown in FIG. 34, the stopper 460 and plunger rod 440 may occupy the chamber of the barrel 420 with the distal end 461 of the stopper face positioned against the distal wall of the barrel 422. Further, the sealing edge 462 of the stopper 460 forms a seal with the interior surface of the barrel 420. As shown, the retaining ring 447 of the stopper-engaging portion 446 retains the stopper 460. As will be more fully described with reference to FIG. 40, the connection between the retaining ring 447 and stopper-engaging portion 446 may be frangible.

Embodiments of the syringe assembly 400 may also include visual markers as described with reference to FIGS. 13-16. In a specific embodiment, the barrel 420 of one or more embodiments can also include a visual marker aligned with the locking rib 423. In a more specific embodiment, the syringe assembly can include a visual indicator disposed on the stopper body 464.

Referring now to FIGS. 34-35, a defined space between the stopper 460 and the distal end of the main body 448 defining a pre-selected axial distance 432. In one or more embodiments, the distance between the flexible protrusion 444 and the sealing edge 462 of the stopper 460 defines a first distance, D1.

Figure 36:
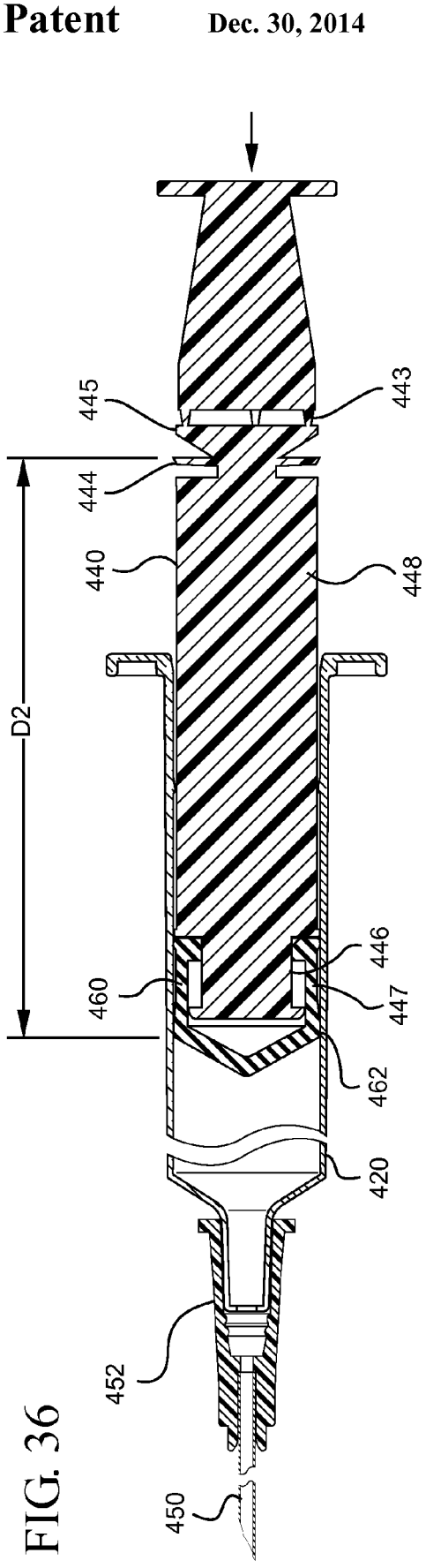
FIG. 36 is an illustration of FIG. 35 showing the plunger rod being moved in the distal direction.

The aspiration or filling step, the injection step and the locking step is shown in FIGS. 35-38. As with the embodiments of FIGS. 7-11, 14-16 and 22-24, when the user applies a force to the plunger rod in the proximal direction, the plunger rod 440 and the stopper 460, joined by the neck 463 and retaining ring 447, move together in the proximal direction as indicated by the arrow. As shown in FIG. 35, the space defining the pre-selected axial distance 432 and the first distance D1 is maintained as the stopper 460 and plunger rod 440 move together in the proximal direction. FIG. 36 shows the syringe assembly 400 when distal force is applied to the plunger rod 440 during an injection step. This force causes the plunger rod 440 to move the pre-selected axial distance 432 shown in FIG. 34 while the stopper 460 remains stationary. This closes the space between the plunger rod 440 and stopper 460 as the plunger rod 440 moves into the interior recess 468. Application of a continuous force in the distal direction to the plunger rod causes the stopper 460 and the plunger rod 440 to move in tandem in the distal direction.

During and after the contents of the syringe have begun to be or have been fully expelled, the distance between the flexible protrusion 444 and the sealing edge 462 defines a second distance, D2, wherein D2 is the difference between the first distance, D1, and the space defining a pre-selected axial distance 432.

As described otherwise herein, the user of the syringe assembly 400 may inject a limited amount of the fluid aspirated or exert a limited force on the plunger rod in the distal direction to flush or expel some of the aspirated fluid, without locking the plunger rod, provided that the syringe assembly is not bottomed.

Figure 37:
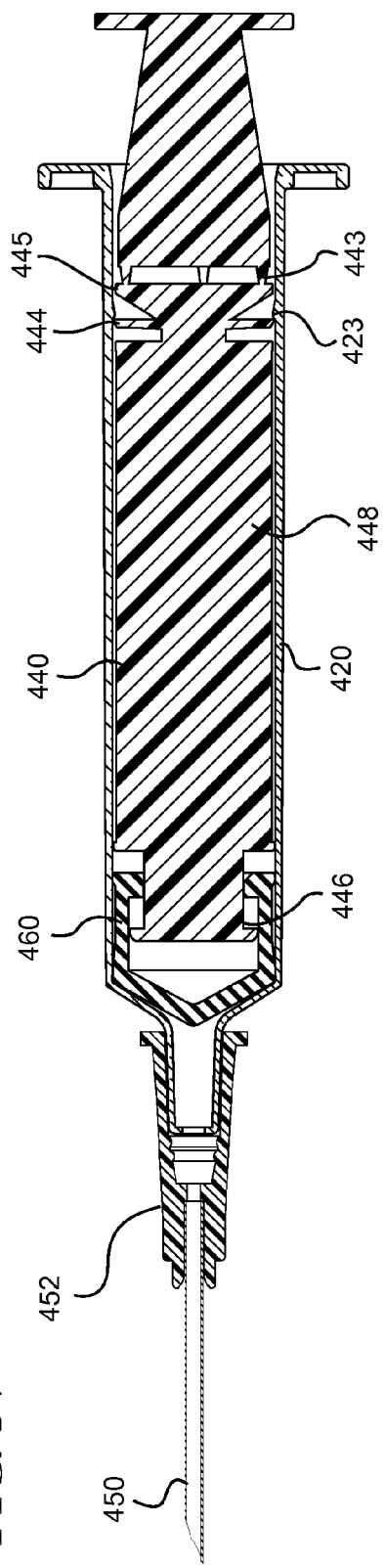
FIG. 37 is an illustration of FIG. 36 showing the plunger rod in a locked position in the syringe barrel.
Figure 38:
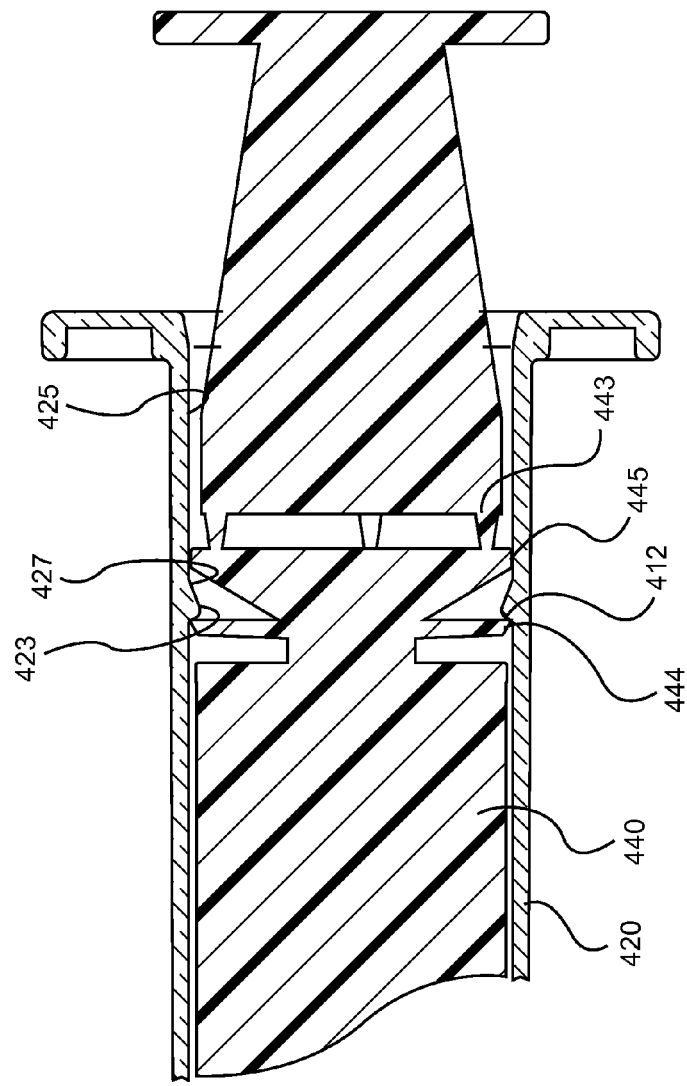
FIG. 38 is an enlarged view of a proximal portion of the assembly shown in FIG. 37.

Referring now to FIGS. 37-38, which illustrate the syringe assembly after the plunger rod 440 has been locked inside the barrel 420, the distal movement of the stopper-engaging portion 446 relative to the stopper 460 closes the gap defining the pre-selected axial distance and allows the flexible protrusion 444 to advance past the rib 423, thereby locking the plunger rod 440 inside the barrel 420, preventing re-use of the syringe assembly.

According to one or more embodiments, the flexible protrusion 444 permits the plunger rod to bottom during normal use of the syringe assembly. Specifically, the flexible protrusion 444 flexes as it moves past the narrowed diameter of the rib 423 of the barrel. In one or more embodiments, as the protrusion 444 moves distally past the rib 423, a slight increase in force may be applied to the plunger rod. According to the embodiment shown, this slight increase in force applied to the plunger rod is not perceptible to a user during normal use of the syringe. Further, the ramp 427 of the barrel facilitates movement of the flexible protrusion 444 past the rib 423. After the flexible protrusion 444 has advanced distally past the rib 423, the distal portion of the rib 412 restricts movement of the flexible protrusion 444 in the proximal direction. It is believed that the activation force, as defined herein, is less than the force required to withdraw the plunger rod.

Figure 39:
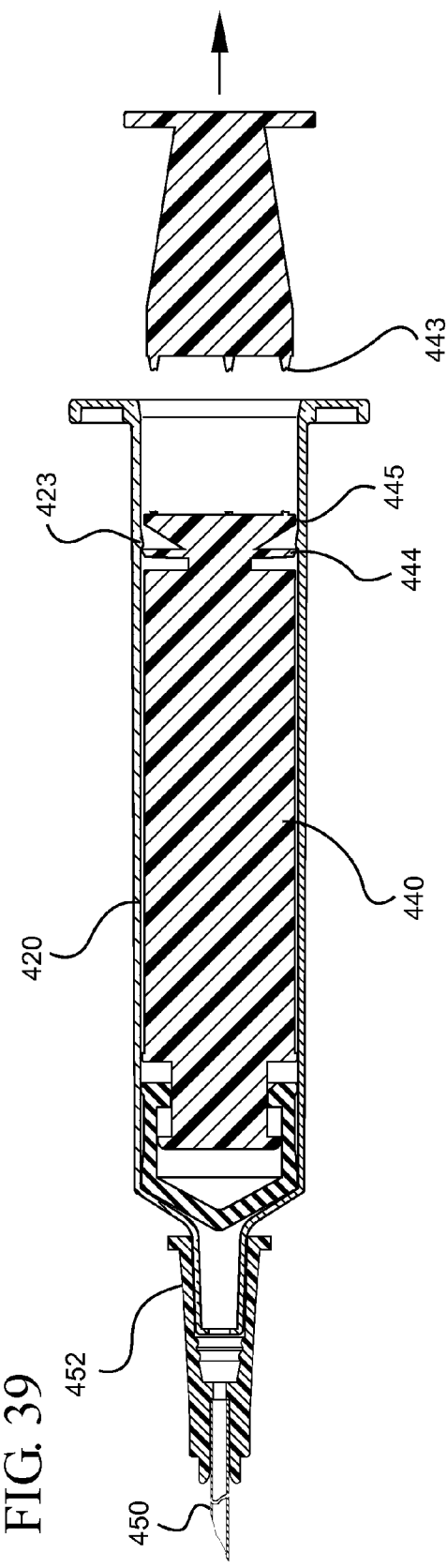
FIG. 39 is an illustration of FIG. 37 showing a proximal portion of the plunger rod being broken from the syringe assembly after the plunger rod has been locked in the barrel.

Referring now to FIG. 39, the syringe assembly 400 is shown in a configuration in which a user attempts to reuse the syringe assembly after the plunger rod 440 is locked inside the barrel 420 by applying a withdrawal force, as defined herein, to the plunger rod 440 in the proximal direction. Application of sufficient proximal force to the plunger rod 440 causing a portion of the plunger rod 440 to separate at the plurality of frangible connections 443, as the withdrawal force exceeds the deactivation force needed to separate a portion of the plunger rod from the body or break the plurality of frangible connections or bridges.

Figure 40:
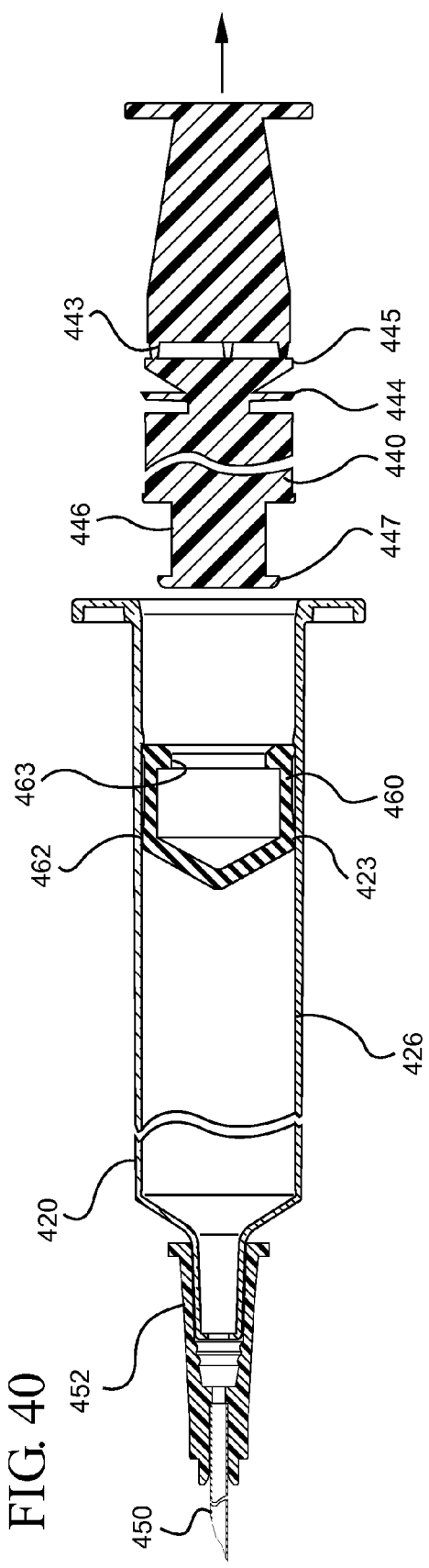
FIG. 40 is an illustration of FIG. 34 showing the plunger rod being moved in the proximal direction and the stopper disengaging from the plunger rod.

FIG. 40 shows the syringe assembly 400 in a configuration after which proximal force has been applied to the plunger rod and the stopper has moved to the proximal end of the barrel. As otherwise described herein, the sealing edge of the stopper 462 has an outer diameter greater than the inner diameter of the interior surface of the barrel at the location of the rib 423 and therefore, application of a force in the force in the proximal direction causes the stopper 460 to separated from the stopper-engaging portion 446 of the plunger rod According to one or more embodiments, the syringe barrel may include identifying information on the syringe assembly. Such information can include, but is not limited to one or more of identifying information regarding the contents of the syringe assembly or information regarding the intended recipient.

Figure 41:
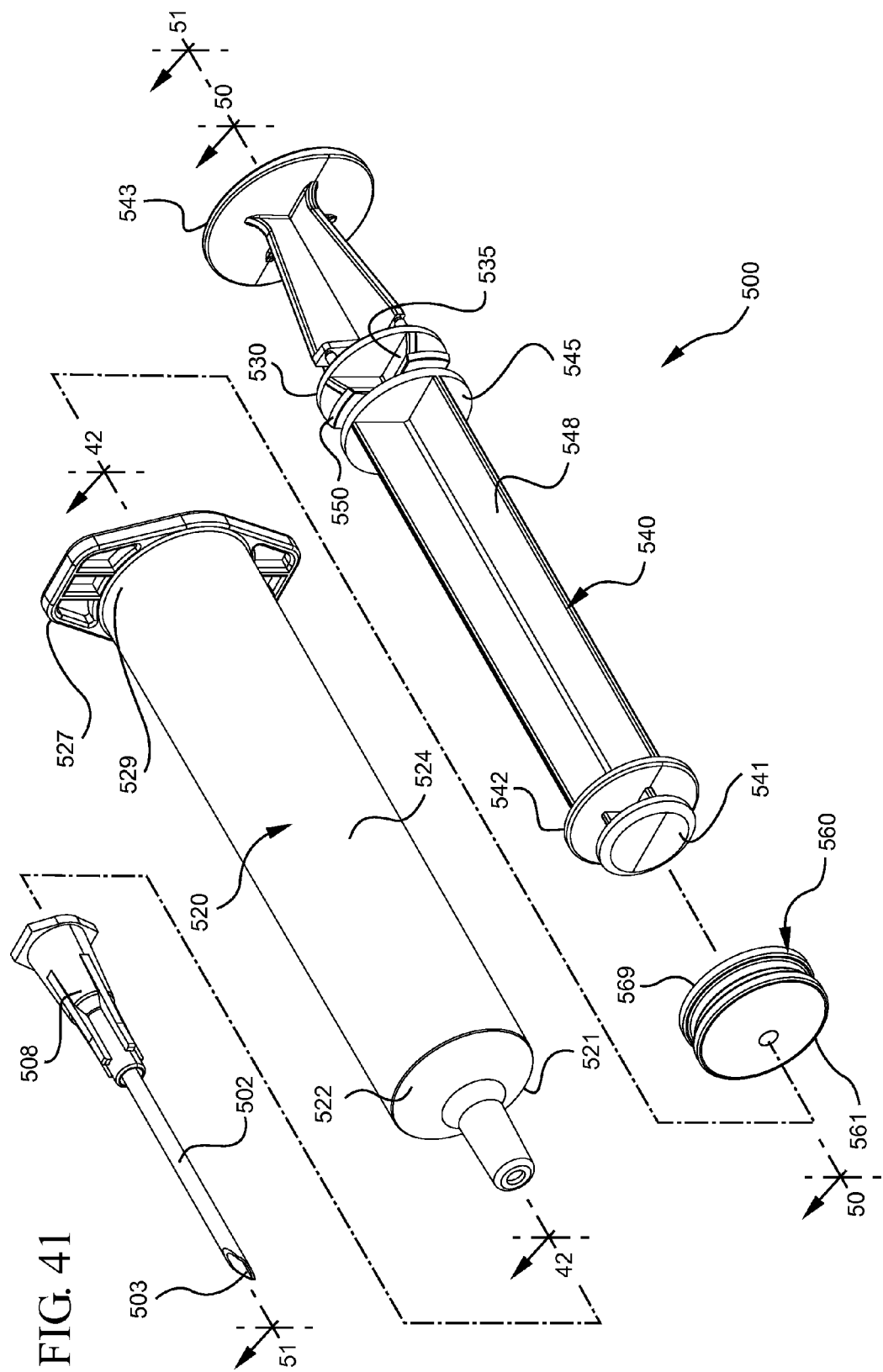
FIG. 41 illustrates a disassembled perspective view of a syringe assembly according to another embodiment of the invention.

FIG. 41 shows an example of a syringe assembly 500 according to another aspect of the present invention. In the embodiment shown in FIG. 41, the assembly includes a barrel 520, a plunger rod 540 and a stopper 560, arranged so that the proximal end 569 of stopper is attached to the distal end 541 of the plunger rod. The assembled stopper 560 and plunger rod 540 are inserted into the proximal end 529 of the barrel 520 for use.

Figure 42:
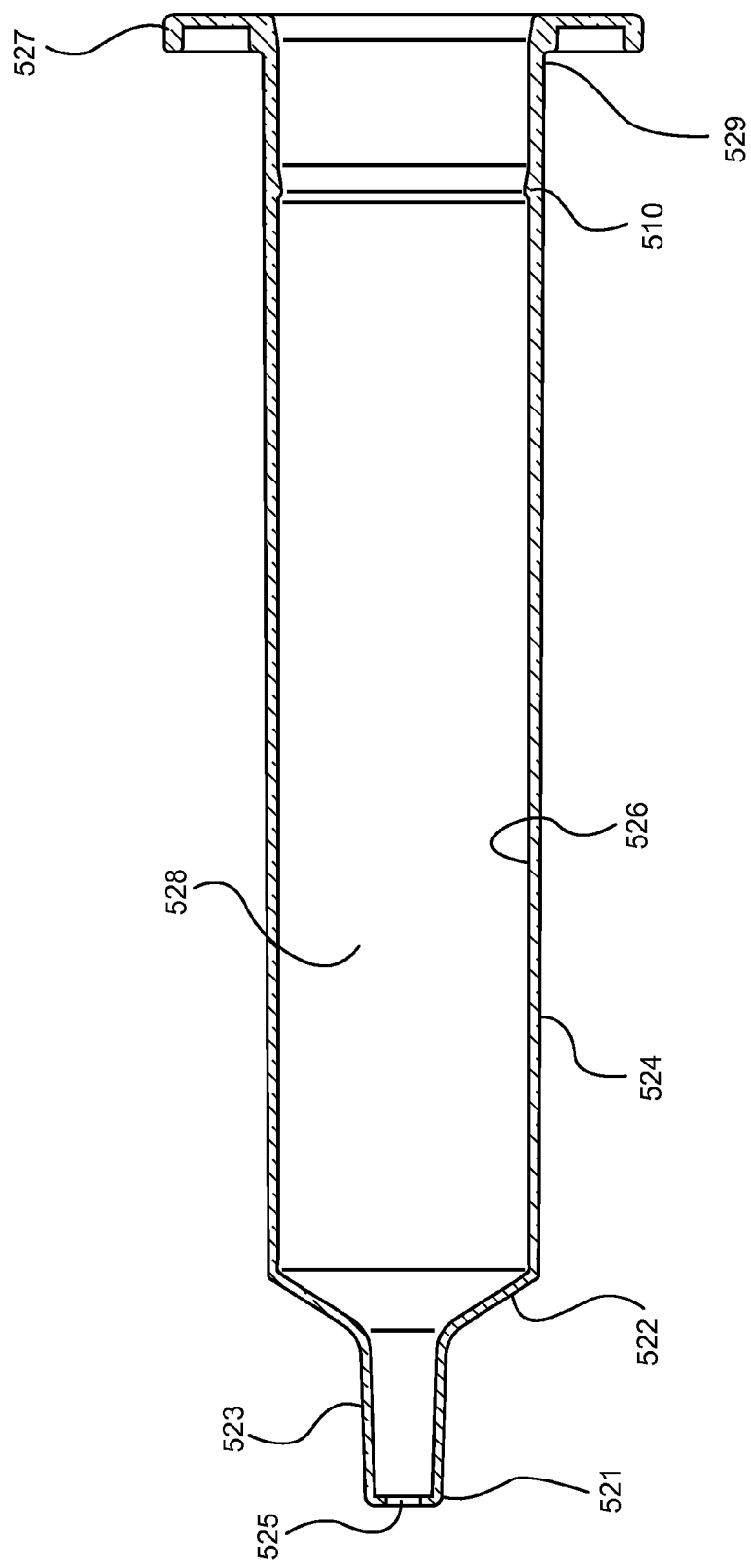
FIG. 42 shows a cross-sectional view of the barrel shown in FIG. 41 taken along line 42-42.

As shown more clearly in FIG. 42, the barrel 520 includes an open proximal end 529 and a distal end 521 and a distal wall 522. A sidewall 524 extends from the distal end 521 to the open proximal end 529 and includes an inside surface 526 that defines a chamber 528 for retaining or holding fluids, which may include liquid medication and/or other liquids. The distal end 521 may also include a tip 523 having an open passageway 525 therethrough in fluid communication with the chamber 528. The barrel may also include a flange 527 attached at the proximal end 529 of the barrel 520 and may also optionally include a needle cannula 502 having a lumen 503 attached to the opening in the distal wall 522 at the distal end 521 of the barrel 520. One or more embodiments also include an attachment hub 508 for attaching a needle cannula to the barrel 520, as shown in FIG. 41.

The barrel further includes a rib 510, locking rib or other means for locking the plunger rod 540 within the barrel 520. In the embodiment shown, the rib 510 defines an interior surface having a cross-sectional width that is smaller than the cross-sectional width of the inside surface 526 of the sidewall 524 of the barrel. In one or more alternative embodiments, the rib 510 may have an alternative configuration, shape or size that prevents the plunger rod from being removed from the barrel 520 or to lock the plunger rod 540 within the barrel. For example, in the embodiment shown in FIG. 42, the rib 510 is formed along the inside surface 526 of the barrel and extends to form an annular wall that projects or extends radially into the chamber 528. In other embodiments, the rib 510 may include a single or more than one protrusion (not shown) that extends into the chamber 528.

Figure 54:
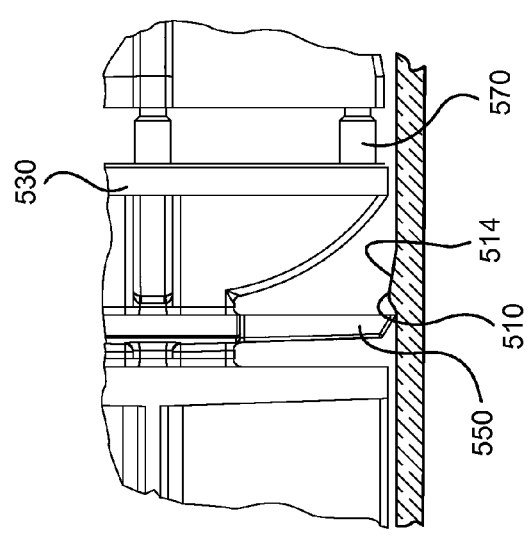
FIG. 54 is an enlarged view of the syringe assembly shown illustration of FIG. 53.

In one or more embodiments, the distal end of the rib 510 may include a distal portion (not shown) facing the distal end 521 of the barrel, as shown in FIGS. 42 and 54. The distal portion (not shown) defines rapid decrease in the cross-sectional width in the inside surface 526 of the barrel to form a barrier to removal of the plunger rod 540. The distal portion (not shown) may also be described as a perpendicular wall that forms a barrier to removal of the plunger rod 540 from the barrel. A ramp (not shown) may be disposed proximally adjacent to the rib 510 having an increasing cross-sectional width from the rib 510 to the open proximal end 529 of the barrel. An increased cross-sectional width region (not shown) may also be disposed proximally adjacent to the ramp (not shown). The increased cross-sectional width region (not shown) may have the same or larger cross-sectional width than the inside surface 526 of the barrel. The ramp (not shown) and/or the increased cross-sectional width region (not shown) would facilitate movement of the plunger rod 540 in the distal direction past the rib 510.

The stopper 560 includes a distal end 561 and a proximal end 569, as more clearly shown in FIG. 41. Shown in FIG. 52, the stopper 560 includes a sealing edge 562 which forms a seal with the inside surface 526 of the barrel. In one or more embodiments, the sealing edge 562 may have a cross-sectional width that is greater than the cross-sectional width of the interior surface of the rib 510. Shown in FIG. 50, the distal end 561 of the stopper includes a stopper face 563 adjacent to the sealing edge 562. The stopper 560 can further include a stopper body 564 defining an interior recess and a neck 568 disposed at its proximal end 569. The stopper may be formed from an elastomeric or plastic material or other material known in the art. When assembled with the plunger rod, a portion of the plunger rod 540 is inserted into the interior recess of the stopper and the neck 568 engages the plunger rod 540, as more clearly shown in FIG. 50. In one or more embodiments, the connection between the plunger rod 540 and the stopper 560 may be frangible, as described with reference to FIGS. 1-40.

Figure 45:
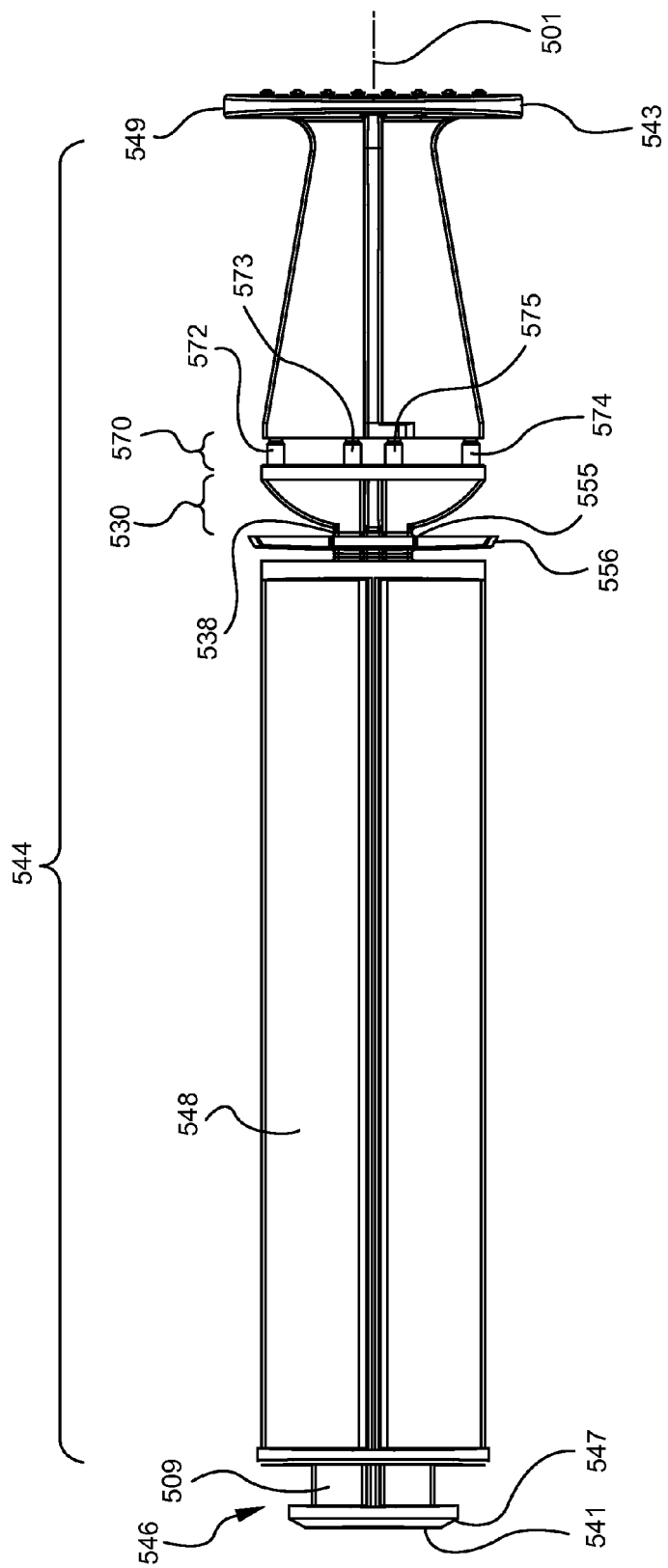
FIG. 45 illustrates a side elevational view of the plunger rod shown in FIG. 41.

Referring now to FIG. 45, the plunger rod 540 is shown as having a plunger rod body 544, which includes a main body 548. The plunger rod body 544 extends from a distal end 541 and a proximal end 549 and is aligned along a first axis 501. The plunger rod 540 further includes a thumb press 543 at its proximal end 549 and a stopper-engaging portion 546 at its distal end 541.

Figure 43:
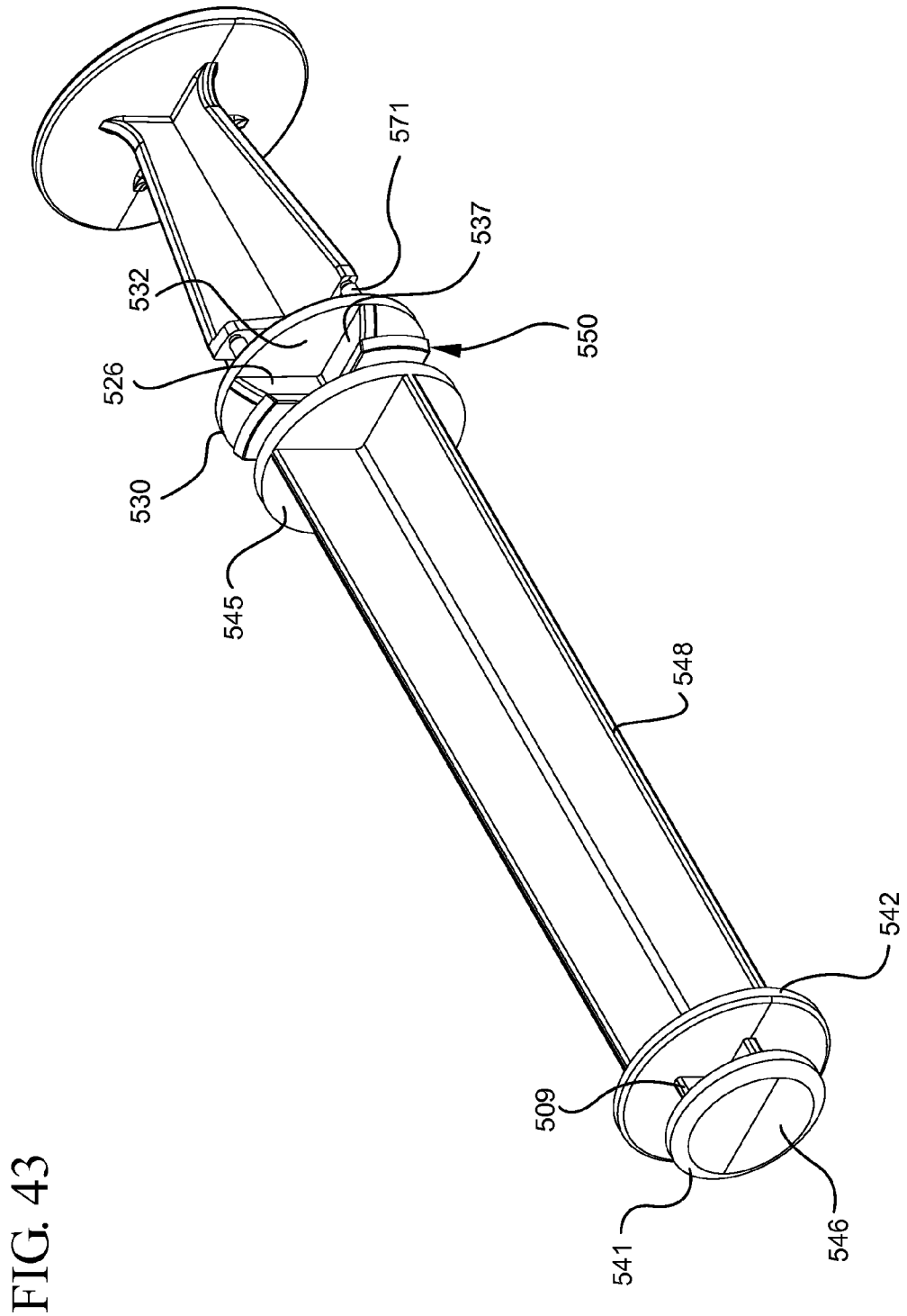
FIG. 43 illustrates a perspective view of the plunger rod shown in FIG. 41 from a distal end.
Figure 44:
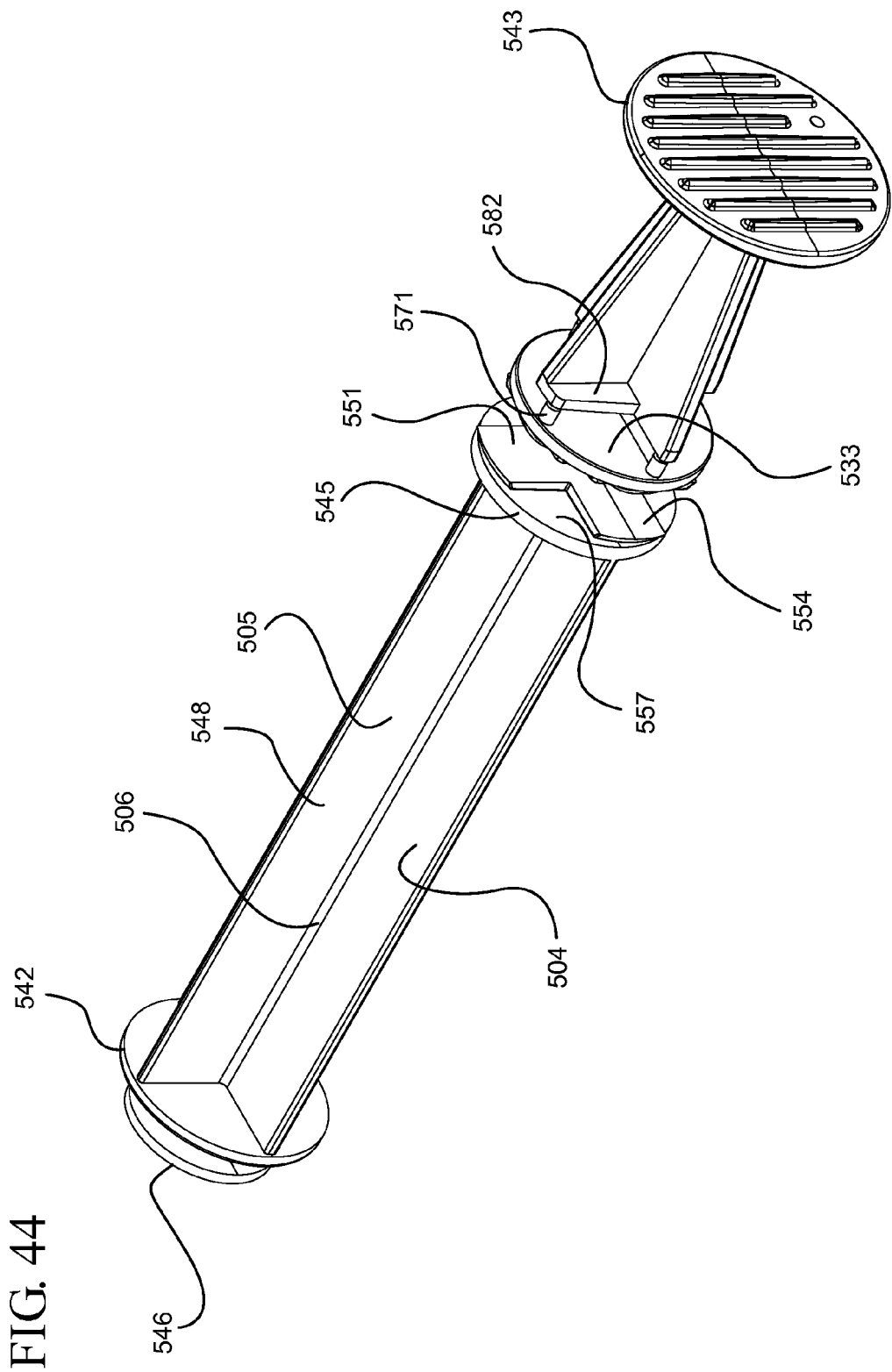
FIG. 44 illustrates a perspective view of the plunger rod shown in FIG. 41 from a proximal end.

The plunger rod body 544 shown in FIGS. 43-45 includes two transverse members 504, 505 which intersect to form a cross-shaped body that defines four quadrants 506 between the two transverse members 504, 505. The transverse members 504, 505 and the quadrants 506 extend from the distal end 541 to the proximal end 549 of the plunger rod and are intersected by a flexible protrusion 550, support 530 and frangible portion 570, as will be described below in greater detail and as shown more clearly in FIG. 45. The dimensions of the transverse members 504, 505 may vary along the length of the plunger rod body 544. For example, as shown in FIG. 45, the cross-sectional width of the transverse members 504, 505 decreases adjacent to the proximal end 549 of the thumb press, decreasing the cross-sectional width of the plunger rod body 544. In one or more embodiments, the plunger rod body 544 may be formed from a single member (not shown), which may be shaped to have a cylindrical cross-section (not shown).

Figure 50:
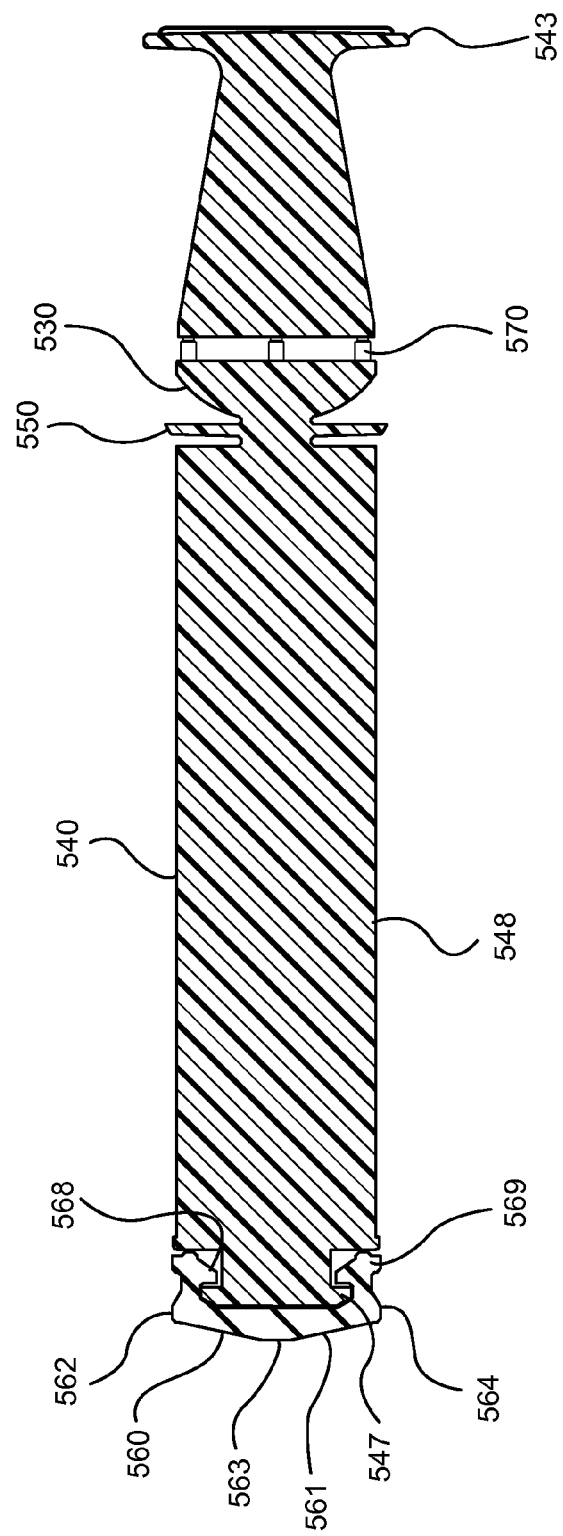
FIG. 50 shows a cross sectional view of the plunger rod shown in FIG. 41 attached to the stopper shown in FIG. 41 taken along lines 50-50.

The stopper-engaging portion 546 shown in FIG. 45 includes a retaining ring 547 for engaging the neck 568 of the stopper 560 to the distal end 541 of the plunger rod. In the embodiment shown in FIG. 45, stopper-engaging portion 546 may include an extending portion 509 disposed between the retaining ring 547 and the main body 548 of the plunger rod. As shown in FIG. 50, the extending portion 509 enables engagement between the neck of the stopper 568 and the retaining ring 547 by accommodating or occupying the interior recess of the stopper 560. In the embodiment shown, the retaining ring 547 has a radially outwardly projection that defines a cross-sectional width that is larger than the cross-sectional width of the interior recess of the stopper 560 at the neck 568. The stopper may optionally include a corresponding structure for engaging the retaining ring 547 of the stopper-engaging portion 546. At least one embodiment of the invention includes a press-fit attachment or other suitable means for retaining or engaging the end of the stopper 560 to the plunger rod 540.

In the embodiment shown in FIG. 41, the plunger rod 540 includes a first disc 542 disposed proximally adjacent to the stopper-engaging portion 546 of the plunger rod or at the distal end of the main body 548. The first disc 542 defines a cross-sectional width that is larger than the cross-sectional width of the interior surface of the rib 510. The first disc 542 is shown having a circular cross-section however it may also have a cross-section that has a square, triangular or other shape. In one or more embodiments, the first disc 542 may have one or more protuberances (not shown) that extend radially outwardly and increase the cross-sectional width of the first disc 542. The plunger rod may further include an optional second disc 545 disposed at the proximal end of the main body 548. The first disc 542 and/or the second disc 545 provide additional stability and may have alternate shapes, depending on the shape of the barrel and/or plunger rod.

Figure 46B:
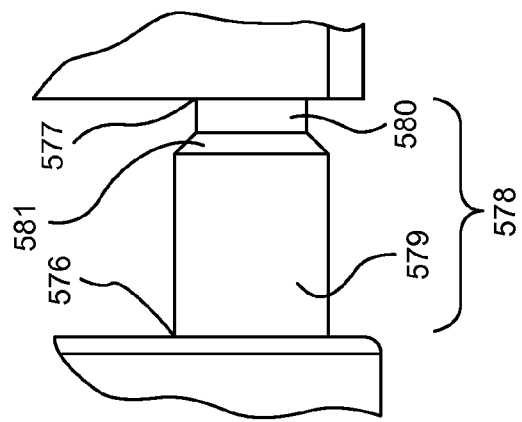
FIG. 46B illustrates an enlarged partial view of the plunger rod shown in FIG. 46A.
Figure 46A:
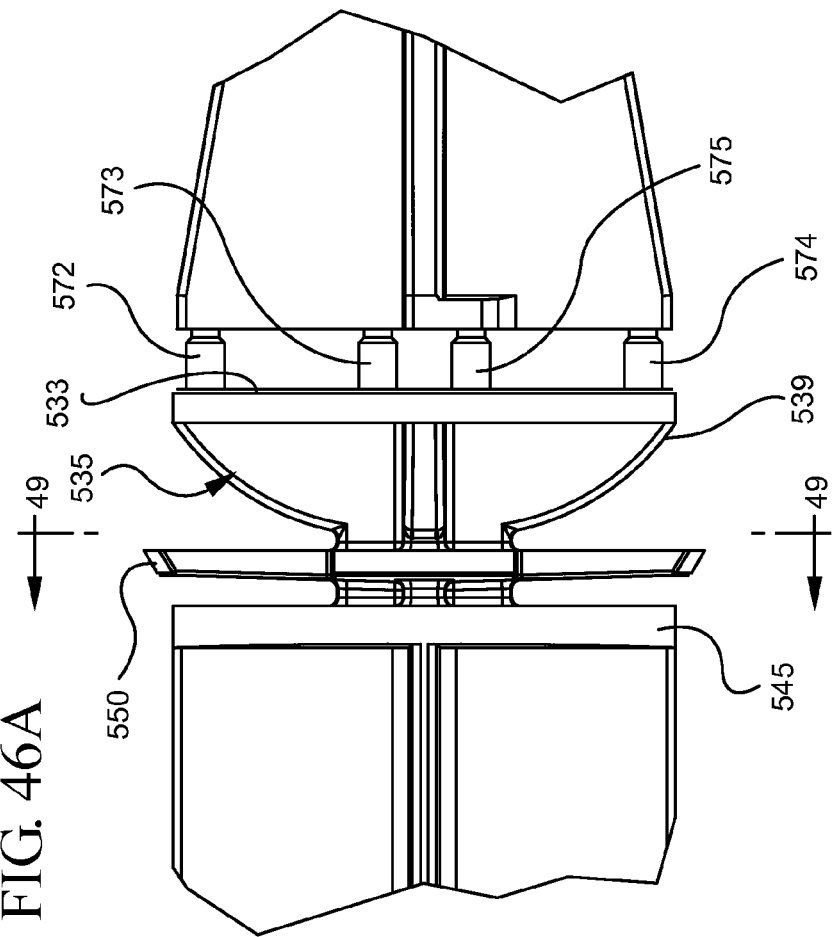
FIG. 46A shows an enlarged partial view of the plunger rod shown in FIG. 45.
Figure 46C:
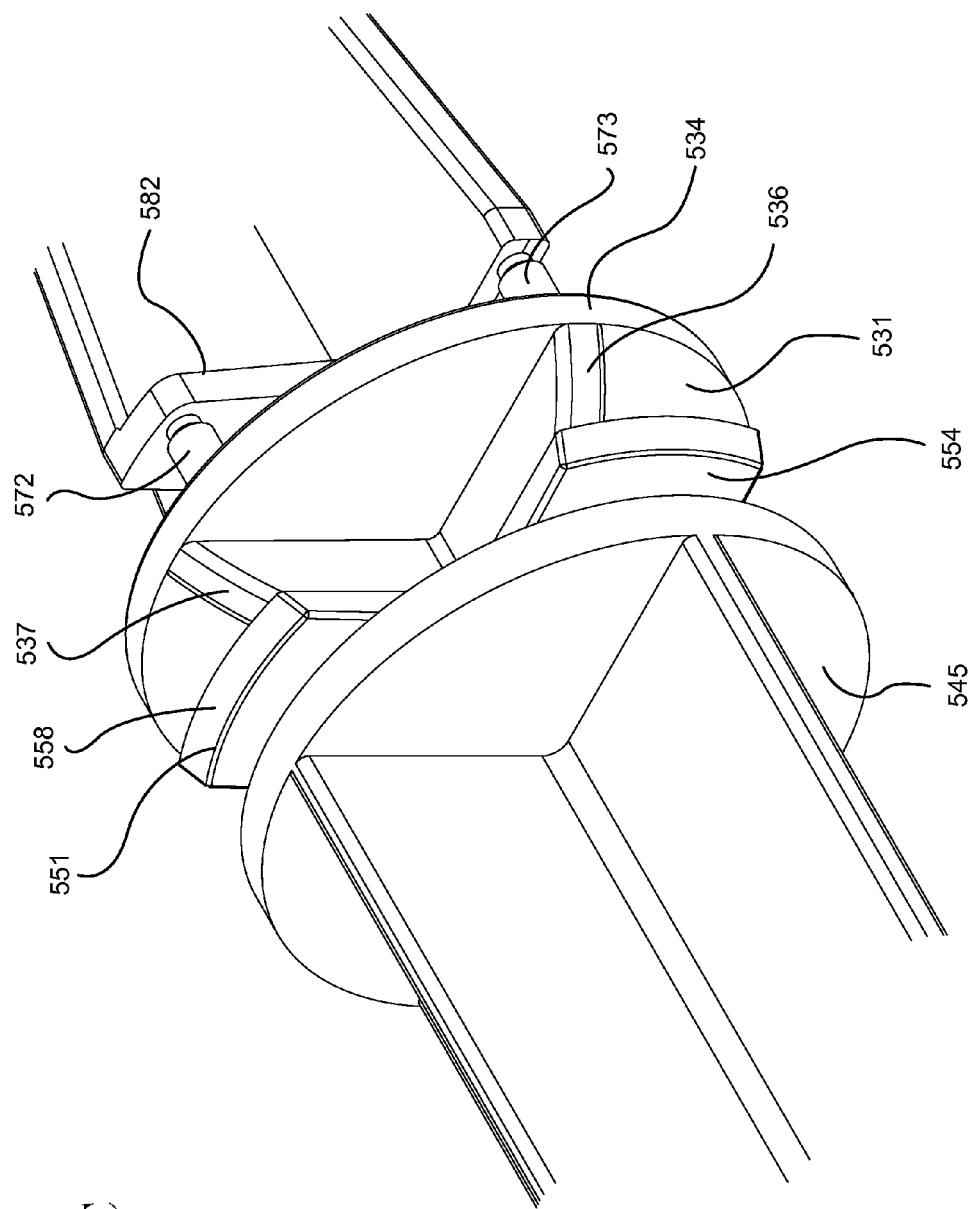
FIG. 46C illustrates an enlarged partial view of the plunger rod shown in FIG. 43.
Figure 49:
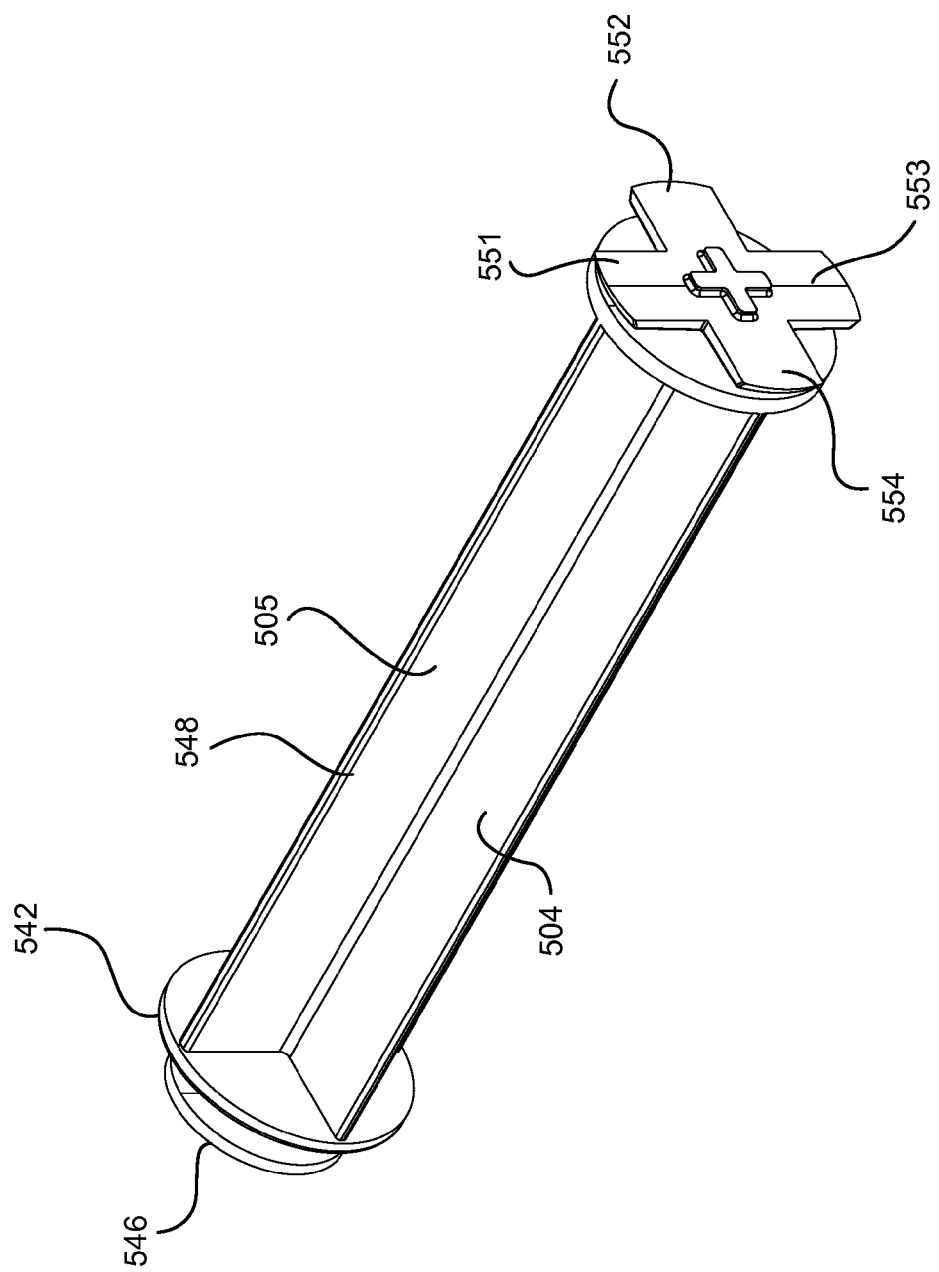
FIG. 49 illustrates a partial perspective view of a portion of the plunger rod shown in FIG. 45 proximally adjacent to the annular projection.

The plunger rod 540 also includes a flexible protrusion 550 disposed between the thumb press 543 and the main body 548. As specifically shown in FIGS. 45, 46A, the protrusion 550 intersects the plunger rod body 544 proximally adjacent to the second disc 545 and/or the main body. The flexible protrusion 550 extends radially outwardly from the plunger rod 540 and is perpendicularly disposed in relation to the first axis 501. The flexible protrusion 550 has an outer cross-sectional width that is greater than the cross-sectional width of the interior surface of the rib 510. As will be described below, the configuration of the syringe assembly allows for the flexible protrusion 550 to advance distally past the rib 510, to lock the plunger rod 540 in the barrel 520, when the user bottoms the syringe assembly or expels all of the contents of the barrel 520 (as more clearly shown in FIGS. 53-55 and discussed further below). The flexible protrusion 550 facilitates distal movement of the plunger rod 540 past the rib 510 by flexing in the proximal direction as a force in the distal direction is applied to the plunger rod. In other words, as the contents of the barrel 520 are being expelled by application of a distally directed force on the plunger rod causing the plunger rod 540 to move in the distal direction through the chamber 528, the protrusion 550 flexes inwardly as it interacts with the rib 510, to allow the stopper 560 to contact the inside surface 526 of the syringe barrel at the distal wall 522, which is more clearly shown in FIGS. 51-52. If the stopper 560 is in contact with the inside surface 526 of the syringe barrel at the distal wall 522, the protrusion 550 will have advanced distally past the rib 510.

In the embodiment shown, the protrusion 550 has a structure which allows it to flex in the proximal direction as it moves distally past the rib 510. In the embodiment shown in FIGS. 46A, 49, 51, 52, and 53, the protrusion 550 includes four radially outwardly extending leaves 551, 552, 553, 554. The leaves 551, 552, 553, 554 include an attachment portion 555 that attaches each of the leaves to the plunger rod body 544. The leaves 551, 552, 553, 554 also each include an unattached or free portion 556 on the end opposite the attachment portion 554. The leaves 551, 552, 553, 554 are attached to the plunger rod 540 and extend perpendicularly or radially outwardly from the plunger rod at the attachment portion 555. The free portion 556 can be described as being unattached to any structure and as providing the leaves 551, 552, 553, 554 with a cantilevered structure. In one or more embodiments, the portion between the attachment portion 555 and the free portion 556 curves outwardly from plunger rod 540 toward the proximal end 549 of the plunger rod such that each of the leaves has an arcuate shape (not shown). The free portion 556 may also include a tapered edge 558 that facilitates movement of the flexible protrusion 550 distally past the rib 510. As will be described below in greater detail, the arcuate shape of the leaves 551, 552, 553, 554 inhibits the flexible protrusion 550 from flexing inwardly after the plunger rod 540 has been locked in the barrel 520. In one or more embodiments, the leaves 551, 552, 553, 554 have spaces 557 between each of the leaves. The spaces 557 are shown as having a triangular shape, with two sides being defined by two leaves and a third open side disposed between the two leaves and opposite the attachment portion 555.

In one or more alternative embodiments, the flexible protrusion 550 may have the shape of a Belleville washer or a disc having a conical shape (not shown), wherein the attachment portion or portion attached to the plunger rod is distally adjacent to the free portion or portion that is unattached to the plunger rod. In one or more alternative embodiments, the flexible protrusion 550 may have a shape of a planar disc (not shown) that is aligned perpendicularly to the plunger rod 540.

The planar disc (not shown) may include a free portion (not shown) that has a tapered edge (not shown) for facilitating movement in the distal direction past the rib 510.

In one or more embodiments, a support 530 is disposed proximally adjacent to the flexible protrusion 550 and intersects the plunger rod body 544. The support 530 may provide additional stability to the plunger rod 540 and syringe assembly 500 during use. In one or more embodiments, the support 530 is disposed perpendicularly to the plunger rod 540 and includes an annular projection 531 having a distally facing surface 532, a proximally facing surface 533 and an outer edge 534. In the embodiment shown, the support 530 includes a strut element 535 disposed on the distally facing surface 532 between the flexible protrusion 550 and the annular projection 531. The strut element 535 includes two beams 536, 537 that extend in the distal direction from the distally facing surface 532 along the first axis 501. The beams 536, 537 intersect one another at the midpoints thereof to form an intersection 538. The beams 536, 537 may be aligned with the transverse members 504, 505 of the plunger rod body 544. The strut element 535 in the embodiment shown is attached to the flexible protrusion 550 at the intersection 538. The beams 536, 537 shown in FIG. 46A have a rounded edge 539 which has a height that increases from the outer edge 534 of the annular projection 531 to the intersection 538.

In one or more alternative embodiments, the support 530 may include an annular projection 531 with a domed body (not shown) attached to the distally facing surface 532 instead of a strut element 535. In other words, the space between the beams 536, 537 may be eliminated such that the strut element has a domed shape (not shown). Optionally, the annular projection 531 of the support 530 may have an increased thickness (not shown) and the strut element may be eliminated such that the support 530 has a generally disc-shaped configuration (not shown).

As shown in FIG. 45, the plunger rod 540 further includes a frangible portion 570. The frangible portion 570 is shown in the embodiment of FIG. 45 as including a plurality of point connections 571 or bridges disposed adjacent to the support 530. In one or more alternative embodiments, the frangible portion 570 may include other structure that permits a portion of the plunger rod 540 to break. In the embodiment shown, the plurality of point connections 571 of the plunger rod 540 is located between the support 530 and the thumb press 543, but the frangible portion 570 could be in another location.

The plurality of point connections 571 may be described as connecting the support 530 to the proximal end 549 of the plunger rod. In the Figures, the plurality of point connections 571 are disposed on the proximally facing surface 533 of the annular projection 531 and connect the support 530 to the thumb press 543 and remaining portion of the plunger rod 540 adjacent to the proximal end 549 of the plunger rod. In the embodiment shown in FIG. 45, the frangible portion 570 includes four point connections 572, 573, 574, 575. In one or more embodiments, the frangible portion 570 may include one, two, three or more than four point connections (not shown). The point connections 571 are distributed such that they are dispersed across the proximally facing surface 533 to provide stability the plunger rod 540 during use, despite the relatively small dimensions of the plurality of point connections 571, which will be described below.

The plurality of point connections 571 include a distal end 576 and a proximal end 577 with a body portion 578 extending from the distal end to the proximal end, the body portion. In the embodiment shown, the body portion 578 of the plurality of point connections 571 has a circular cross-section defining a cross-sectional width. Optionally, the body portion 578 of the plurality of point connections 571 may have a cross-section having a different shape, for example, square, triangular or other suitable shapes.

In one or more embodiments, the cross-sectional width of the body portion 578 of the plurality of point connections 571 remains constant from the distal end 576 to the proximal end 577. In one variant, the cross-sectional width of the body portion 578 of the plurality of point connections 571 may decreases from the distal end 576 to the proximal end 577. The cross-sectional width of the body portion 578 of one or more embodiments may increase or decrease from the distal end 576 to the proximal end 577 linearly or incrementally. In the embodiment shown in FIG. 46B, the cross-sectional width of the body portion 578 of the plurality of point connections decreases incrementally from the distal end 576 to the proximal end 577. Specifically, the body portion 578 comprises a distal portion 579 having a first cross-sectional width, a proximal portion 580 having a second cross-sectional width that is less or smaller than the first cross-sectional width. The body portion 578 of the plurality of point connections also includes a transition portion 581 disposed between the distal portion 579 and the proximal portion 580. The transition portion 581 has a transitional cross-sectional width that decreases from the distal portion 579 to the proximal portion 580.

In one or more alternative embodiments, the distal portion 579 and the proximal portion 580 may have substantially the same cross-sectional widths, while the transitional cross-sectional width of the transition portion 581 has a smaller cross-sectional width than the distal portion and the proximal end 577.

The plurality of point connections 571 may include one or more point connections with a constant cross-sectional width, while the remaining point connections have cross-sectional widths that increase or decrease from the distal end to the proximal end or has a decreased cross-sectional width at a transition portion between the distal portion and the proximal portion. Alternatively, one or more of the point connections may include a cross-sectional width that decreases or increases in incrementally or in a stepped fashion, while the remaining point connections may have constant cross-sectional widths, cross-sectional widths that increase or decrease linearly and/or include a decreased cross-sectional width at a transition portion between the distal portion and the proximal portion.

The distance between the point connections 571 may be constant or may vary. In the embodiment shown, the distance between point connection 572 and point connection 574 is larger than the distance between point connection 573 and point connection 575. In such embodiments where the distance between the point connections are not constant, the point connections are disposed in an off-set or staggered manner. For example, in FIG. 46A, point connections 572 and 574 are aligned with transverse members 504, 505 of the plunger rod body 544 and/or the beams 536 and 537 of the support 530, whereas point connections 573 and 575 are disposed slightly to the left of the beams 536 and 537, when viewed from the distal end 541 of the plunger rod. In the embodiment shown in FIG. 46A, off-set elements 582 are incorporated to support the point connections 572 and 574. The off-set elements 582 may extend or project radially outwardly from the transverse members 504, 505 into the openings 506 defined by the transverse members. In the embodiment shown, the off-set elements 582 taper as they extend radially outwardly from the transverse members 504, 505 into the openings 506. The distal ends 576 of the point connections 571 include a collective point connection surface that has a cross-sectional width that is substantially smaller than the surface area of the proximally facing surface 533 of the support 530. In one or more embodiments, the ratio of the surface area of the proximally facing surface 533 to the surface area of the point connections 571 may be greater than about 1:200. In other words, the surface area differential between the point connections 571 and the proximally facing surface 533 is greater than about 200. In a more specific embodiment, the ratio of the surface area of the proximally facing surface 533 to the surface area of the point connections 571 may be greater than about 1:250, or, more specifically, greater than about 1:300. In one or more specific embodiments, the ratio of the surface area of the proximally facing surface 533 to the surface area of the point connections 571 may be in the range from about 1:250 to about 1:350. In one or more specific embodiments, the ratio of the surface area of the proximally facing surface 533 to the surface area of the point connections 571 may be about 1:300.

Embodiments of the syringe assembly 500 may also include visual markers (not show) as described with reference to FIGS. 13-16. In a specific embodiment, the barrel 520 of one or more embodiments can also include a visual marker (not shown) disposed on the sidewall 524 such that it is aligned with the rib 510. In a more specific embodiment, the syringe assembly 500 can include a visual indicator (not shown) disposed on the stopper body 564.

In one or more embodiments, the stopper 560 and the plunger rod 540 may be configured and assembled such that there is relative movement between the stopper 560 and the plunger rod 540, as described above with reference to FIGS. 1-40. In such embodiments, the stopper 560 and the plunger rod 540 may be positioned within the chamber 528 of the barrel 520 such that the stopper face 563 is positioned against or in contact with the distal wall 522 of the barrel.

In the embodiment shown in FIG. 50, the stopper 560 and the plunger rod 540 are assembled in a fixed relationship. In such embodiments, the stopper 560 and plunger rod 540 may occupy the chamber 528 of the barrel with the distal end 561 of the stopper face 563 positioned at a distance from the distal wall 522 of the barrel. The length of the plunger rod 540 and the stopper 560 from the stopper face 563 to the flexible protrusion 550 is shorter than the length between the distal wall 522 of the barrel and the rib 510, enabling the flexible protrusion 550 to move distally past the rib 510 when the stopper face 563 is in contact with the distal wall 522 of the barrel.

Figure 51:
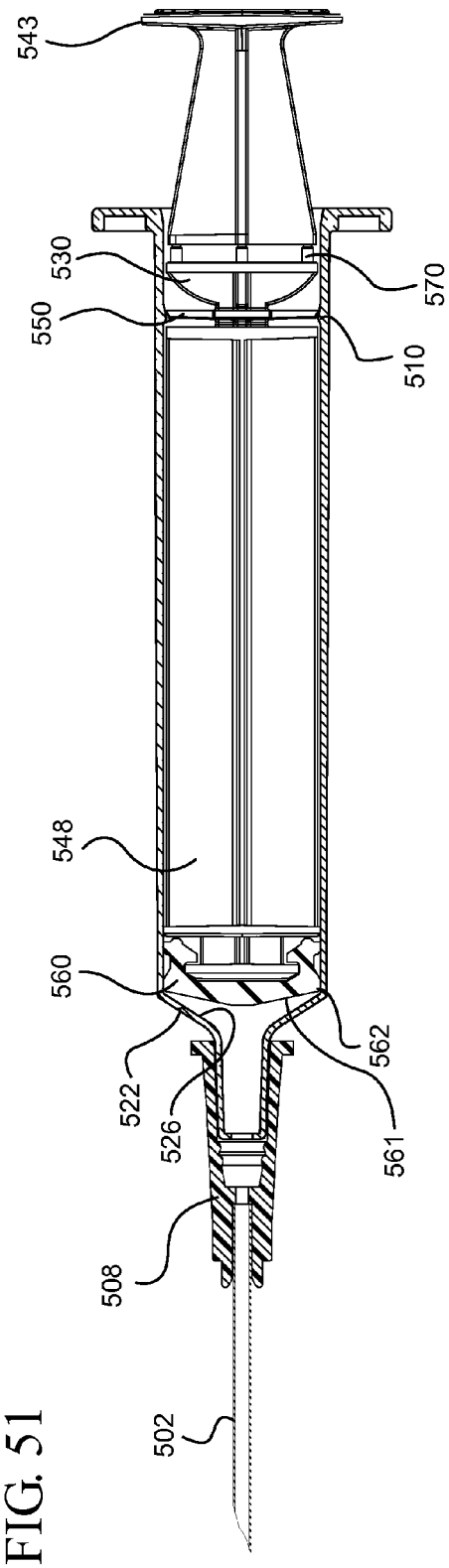
FIG. 51 is a cross-sectional view taken along line 51-51 of the syringe assembly shown in FIG. 41.

As shown in FIG. 51, when the stopper 560 and the plunger rod 540 are initially positioned within the barrel 520, the flexible protrusion 550 is positioned proximally adjacent to the rib 510. In one or more embodiments, the distance between the stopper face 563 and the distal wall 522 of the barrel may be adjusted to position the flexible protrusion 550 to proximally adjacent to the rib 510.

Figure 52:
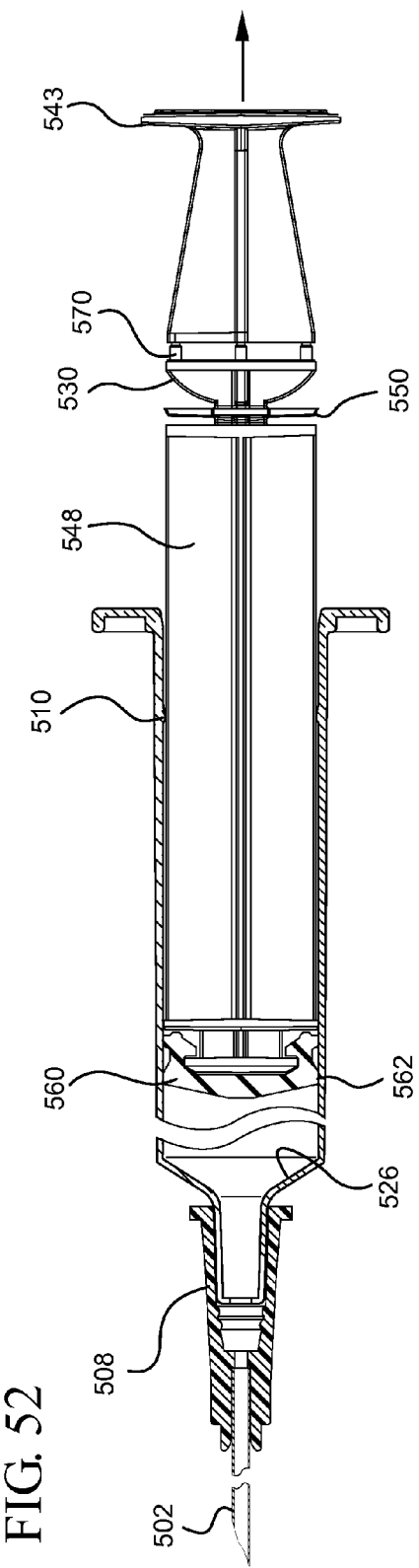
FIG. 52 is an illustration of FIG. 51 showing the plunger rod being moved in the proximal direction.
Figure 53:
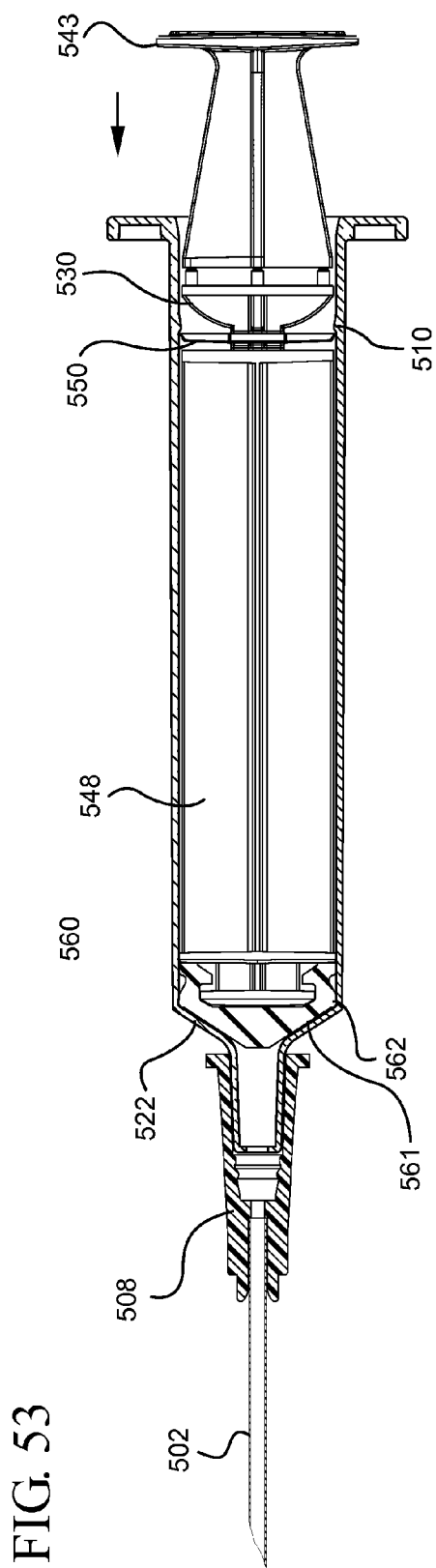
FIG. 53 is an illustration of FIG. 52 showing the plunger rod being moved in the distal direction.

When the user applies a force to the plunger rod 540 in the proximal direction, the plunger rod 540 and the stopper 560, joined by the neck 568 and retaining ring 547, move together in the proximal direction as indicated by the arrow. FIGS. 52-53 show the syringe assembly 500 when continuous distal force is applied to the plunger rod 540 during an injection step. This force causes the plunger rod 540 and the stopper 560 to move in the distal direction until the contents of the chamber 528 of the barrel are expelled and the stopper face 563 is in contact with the distal wall 522 of the barrel. Optionally, the user of the syringe assembly 500 may inject a limited amount of the fluid aspirated or exert a limited force on the plunger rod in the distal direction to flush or expel some of the aspirated fluid, without locking the plunger rod, provided that the syringe assembly is not bottomed.

Figure 55:
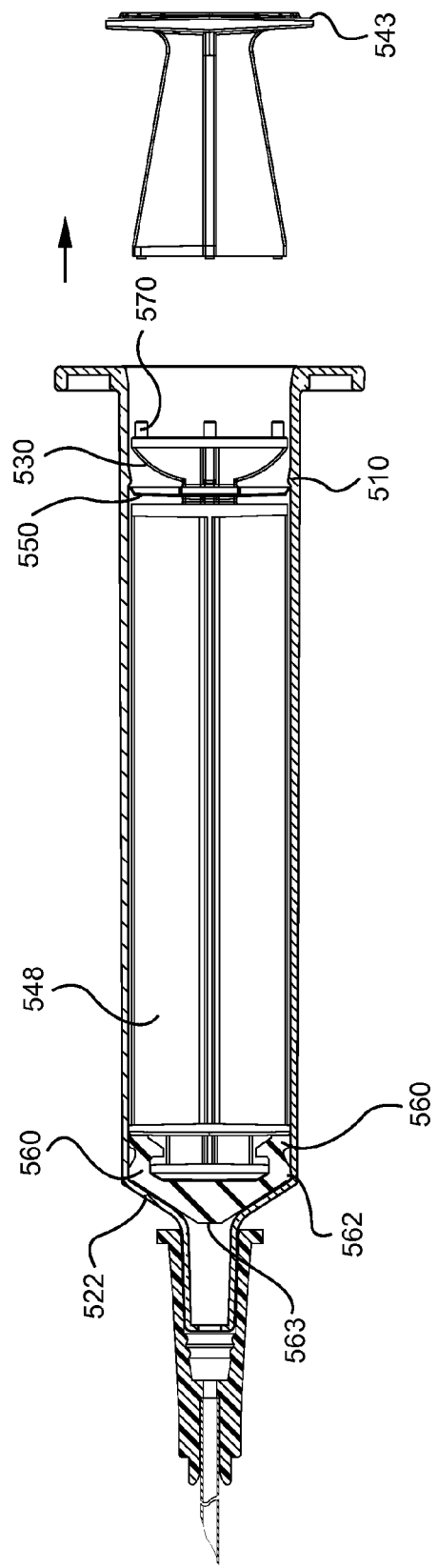
FIG. 55 is an illustration of FIG. 53 showing the plunger rod being broken from the syringe assembly after the plunger rod has been locked in the barrel.

As the entire contents of the barrel 520 are expelled, the flexible protrusion 550 moves distally past the rib 510, as shown in FIGS. 53-55. When the stopper face 563 is in contact with the distal wall 522 of the barrel, the flexible protrusion 550 is positioned distally adjacent to the rib 510 and the plunger rod 540 is locked within the barrel 520.

According to one or more embodiments, the flexible protrusion 550 permits the plunger rod 540 and stopper 560 to bottom during normal use of the syringe assembly. Specifically, the flexible protrusion 550 flexes as it moves past the narrowed cross-sectional width of the rib 510 of the barrel. In one or more embodiments, as the protrusion 550 moves distally past the rib 510, a slight increase in force may be applied to the plunger rod. According to the embodiment shown, this slight increase in force applied to the plunger rod is not perceptible to a user during normal use of the syringe. Further, the ramp 514 of the barrel 520 facilitates movement of the flexible protrusion 550 past the rib 510. It is believed that the activation force, as defined herein, is less than the force required to withdraw the plunger rod. After the flexible protrusion 550 has advanced distally past the rib 510, the rib 510 restricts movement of the flexible protrusion 550 in the proximal direction. In embodiments which incorporate a rib 510 that includes a distal portion (not shown), the distal portions specifically restricts movement of the flexible protrusion 550 in the proximal direction. The arcuate shape of the flexible protrusion 550 also prevents the flexible protrusion 550 to engage the rib 510 in a manner which would enable the flexible protrusion 550 to flex inwardly and release or unlock the plunger rod 540 from the barrel 520.

As is shown in FIG. 53-55, the plunger rod 540 is locked within the barrel 520 without the use of additional force after the fluid has been expelled from the barrel 520 and/or after the stopper 560 is in contact with the distal wall 522 of the barrel. Instead, the flexible protrusion 550 moves distally past the rib 510 as the user bottoms the plunger rod 540 and the stopper 560 within the barrel 520 and/or expels all of the contents of the barrel 520. Accordingly, the syringe assembly 500 provides a passive reuse prevention mechanism that does not require the user to actively lock the plunger rod 540 into the barrel 520.

Referring now to FIG. 55, the syringe assembly 500 is shown in a configuration in which a user attempts to reuse the syringe assembly after the plunger rod 540 is locked inside the barrel 520 by applying a withdrawal force, as defined herein, to the plunger rod 540 in the proximal direction. Application of sufficient proximal force to the plunger rod 540 causes a portion of the plunger rod 540 to separate at the frangible portion 570, as the withdrawal force exceeds the deactivation force needed to separate a portion of the plunger rod from the body or break at least a portion of the plurality of frangible point connections 571 or bridges. In other words, the force exerted by the rib 510 on the leaves 551, 552, 553, 554 of the flexible protrusion 550 exceeds the force required to break the frangible connections 571.

According to one or more embodiments, the syringe barrel may include identifying information on the syringe assembly. Such information can include, but is not limited to one or more of identifying information regarding the contents of the syringe assembly or information regarding the intended recipient.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A syringe assembly comprising:
   a barrel including a cylindrical sidewall having an interior surface with a first cross-sectional width defining a chamber for retaining fluid, an open proximal end and a distal end including a distal wall having an opening therethrough in fluid communication with said chamber, said sidewall including a rib adjacent said proximal end defining a second cross-sectional width that is less than the first cross-sectional width;
   an elongate plunger rod including a proximal end, a distal end, and a main body extending between the proximal and distal end, the plunger rod being distally and proximally movable within said chamber, the proximal end including a thumb press, the distal end including a stopper-engaging portion, the plunger rod further including a flexible protrusion between the thumb press and the main body, the protrusion having a cross-sectional width greater than the cross-sectional width of the barrel at the rib and the plunger rod further including a first support member disposed perpendicularly to the plunger rod that includes an annular projection having a distally facing surface, a proximally facing surface and an outer edge; a strut element disposed on the distally facing surface between the flexible protrusion and the annular projection and at least one frangible portion comprising disposed proximally adjacent to the support member and comprising two or more point connections are disposed adjacent to the edge of the support member, the strut element includes a first beam and a second beam which extend in a distal direction from the distally facing surface along a first axis wherein the first beam and the second beam intersect one another at a midpoint between the first beam and the second beam to form an intersection; the first beam and the second beam have a rounded edge which has a height that increases from the outer edge of the annular projection to the intersection;
   a stopper having a proximal end and a distal end, the stopper attached to the stopper-engaging portion of the plunger rod such that when the distal end of the stopper is in contact with the distal wall of the barrel, the flexible protrusion is permitted to advance distally past the rib in the barrel and lock the plunger rod in the barrel to prevent reuse of the syringe assembly.

2. The syringe assembly of claim 1, wherein the main body of the plunger rod comprises two intersecting transverse members to form a cross-shaped body having four quadrants between the intersecting two transverse members.

3. The syringe assembly of claim 2, wherein the transverse members and the quadrants extend from the distal end to the proximal end of the plunger rod and are intersected by the flexible protrusion, support and frangible portion.

4. The syringe assembly of claim 3, wherein the cross-sectional width of the transverse members decreases from the support to the thumb press.

5. The syringe assembly of claim 1, wherein the strut element is attached to the flexible protrusion at the intersection.

6. The syringe assembly of claim 1, wherein the first beam and the second beam are aligned with the transverse members of the main body of the plunger rod.

7. The syringe assembly of claim 1, wherein a distal end of the rib includes a distal portion facing the distal end of the barrel having a decrease in the cross-sectional width in the interior surface of the barrel to form a barrier to removal of the plunger rod.

8. The syringe assembly of claim 1 further comprising a ramp disposed proximally adjacent to the rib having an increasing cross-sectional width from the rib to the open proximal end of the barrel.

9. The syringe assembly of claim 8, wherein the ramp facilitates advancement of the annular protrusion distally past the rib.

10. The syringe assembly of claim 1, wherein the proximal end of the barrel further comprising a flange.

11. The syringe assembly of claim 1, wherein the barrel further comprising a needle cannula attached to the opening of the barrel.

12. The syringe assembly of claim 1, wherein the connection between the plunger rod and the stopper is frangible.

13. The syringe assembly of claim 1, wherein the flexible protrusion comprises at least two leaves extending radially outwardly from the plunger rod.

14. The syringe assembly of claim 13, wherein the at least two leaves have an arcuate shape that inhibits the flexible protrusion from flexing inwardly after the plunger rod has been locked in the barrel.

15. The syringe assembly of claim 13, wherein the at least two leaves have a tapered outer edge that facilitates movement of the flexible protrusion distally past the rib.

16. The syringe assembly of claim 1, wherein the plunger rod further comprises a second support member disposed at the proximal end of the main body.

17. The syringe assembly of claim 1, wherein the two or more point connections are disposed in an off-set pattern.

18. The syringe assembly of claim 17, wherein the protrusion further includes four leaves disposed such that any two of the four leaves are equidistant from each other and a third point connection and a fourth point connection is misaligned with a third and a fourth leaves, wherein the third point connection and the fourth point connection are disposed adjacent to opposite ends of the outer edge of the support member.

19. The syringe assembly of claim 18, further comprising off-set elements that project radially outward and taper from the transverse members into openings between the transverse members.

20. The syringe assembly of claim 1, wherein the protrusion facilitates distal movement of the plunger rod by flexing in the proximal direction as a force in the distal direction is applied to the plunger rod.

21. The syringe assembly of claim 1, further comprising a gap between the distal end of the stopper and the distal wall of the barrel when the syringe assembly is in an initial position.

22. The syringe assembly of claim 1, wherein the application of a continuous distally directed force to the plunger rod causes the stopper and plunger rod to move together in the distal direction within the barrel until the stopper reaches the distal end of the barrel, thereby allowing the protrusion to advance distally past the rib in the barrel and lock the plunger rod in the barrel to prevent reuse of the syringe assembly.

23. The syringe assembly of claim 1, wherein application of a proximally directed force to the plunger, after the protrusion has advanced distally past the rib, causes the frangible portion of the plunger rod to break.

24. The syringe assembly of claim 1, wherein the two or more point connections are adapted to withstand application of a force on the plunger rod in the distal direction and break upon application of a force in the proximal direction after the flexible protrusion has advanced distally past the rib.

25. The syringe assembly of claim 1, wherein the cross-sectional width of the two or more point connections decreases from the distal end to the proximal end.

26. The syringe assembly of claim 1, wherein the body portion comprises a distal portion having a first cross-sectional width, a proximal portion having a second cross-sectional width that is less than the first cross-sectional width, and a transition portion disposed between the distal portion and the proximal portion, the transition portion having a transitional cross-sectional width that decreases from the distal portion to the proximal portion.

27. The syringe assembly of claim 1, further comprising a visual indicator on the stopper-engaging portion being fully visible when the stopper-engaging portion is proximally moved relative to the stopper.

* * * * *